US009510918B2

(12) United States Patent
Sanchez

(10) Patent No.: US 9,510,918 B2
(45) Date of Patent: Dec. 6, 2016

(54) SYSTEMS AND METHODS FOR CONSOLIDATED MANAGEMENT AND DISTRIBUTION OF ORTHODONTIC CARE DATA, INCLUDING AN INTERACTIVE THREE-DIMENSIONAL TOOTH CHART MODEL

(71) Applicant: Cogent Design, Inc., Marietta, GA (US)

(72) Inventor: Mark Sanchez, Atlanta, GA (US)

(73) Assignee: Cogent Design, Inc., Marietta, GA (US)

( * ) Notice: Subject to any disclaimer, the term of this patent is extended or adjusted under 35 U.S.C. 154(b) by 564 days.

(21) Appl. No.: 13/875,578

(22) Filed: May 2, 2013

(65) Prior Publication Data
US 2013/0297275 A1 Nov. 7, 2013

Related U.S. Application Data

(60) Provisional application No. 61/641,456, filed on May 2, 2012.

(51) Int. Cl.
*G06T 17/00* (2006.01)
*A61C 7/00* (2006.01)
(Continued)

(52) U.S. Cl.
CPC ............. *A61C 7/002* (2013.01); *A61C 7/14* (2013.01); *A61C 7/36* (2013.01); *G06T 19/20* (2013.01);
(Continued)

(58) Field of Classification Search
None
See application file for complete search history.

(56) References Cited

U.S. PATENT DOCUMENTS 6,068,482 A 5/2000 Snow
8,121,718 B2 2/2012 Rubbert et al.
(Continued)

FOREIGN PATENT DOCUMENTS

WO WO 98/53428 A1 11/1998
WO WO 2007/130573 A2 11/2007

OTHER PUBLICATIONS

International Searching Authority, International Search Report and Written Opinion for International Application No. PCT/US2013/039231, Jan. 12, 2015, 10 pages, European Patent Office, The Netherlands.
(Continued)

*Primary Examiner* — Devona Faulk
*Assistant Examiner* — Xilin Guo
(74) *Attorney, Agent, or Firm* — Alston & Bird LLP

(57) ABSTRACT

Various embodiments provide a computer-implemented method for dynamically manipulating a three-dimensional virtual model representing a patient's teeth so as to facilitate visualization of an orthodontic treatment plan being applied thereto. The method comprises: rendering the three-dimensional virtual model based, at least in part, upon one or more images of a patient's teeth, and manipulating the three-dimensional virtual model via a translational movement in a two-dimensional computer display area and along a plane vertically oriented relative to the oppositely-oriented teeth. The translational movement imposes a translational manipulation upon a first one of the two sets of oppositely oriented teeth and a rotational manipulation upon a second one of the two sets of oppositely oriented teeth, the simultaneous manipulation being configured to open the teeth relative to one another so as to facilitate visualization of an orthodontic treatment plan. Associated computer program products and systems are also provided.

29 Claims, 22 Drawing Sheets

(51) Int. Cl.
*A61C 7/14* (2006.01)
*A61C 7/36* (2006.01)
*G06T 19/20* (2011.01)

(52) U.S. Cl.
CPC .... *G06T 2210/41* (2013.01); *G06T 2219/2016* (2013.01)

(56) References Cited

U.S. PATENT DOCUMENTS

| | | |
|---|---|---|
| 2003/0220778 A1 | 11/2003 | Hultgren et al. |
| 2004/0029068 A1* | 2/2004 | Sachdeva et al. ............... 433/24 |
| 2006/0105286 A1* | 5/2006 | Raby et al. ...................... 433/24 |
| 2011/0045428 A1 | 2/2011 | Boltunov et al. |
| 2011/0269097 A1 | 11/2011 | Sporbert et al. |
| 2012/0070803 A1* | 3/2012 | Manai et al. ................. 433/213 |
| 2013/0089828 A1* | 4/2013 | Borovinskih et al. ............ 433/6 |

OTHER PUBLICATIONS

Product Lifecycle Management, "Oracle CADView-3D DeskTop User's Guide, Release 12; Part No. B31983-03", Nov. 2007, 124 pages, ORACLE, USA.

Intellectual Property Office of New Zealand, "First Examination Report for IP No. 702200", Mar. 2, 2015, 4 pages, New Zealand.

* cited by examiner

PATIENT INFO

FIND PATIENT: | NAME, ID, PHONE NUMBER OR POST CODE | | FIND |

| FIRST NAME | MIDDLE NAME | LAST NAME | PATIENT NUM | STREET ADDRESS | PHONE |
|---|---|---|---|---|---|
| MAGGIE | B | MARTINS | 1840 | 3318 E WOOD VALLEY RD NW | 770-777-8716 |
| ANTHONY | | DELEO | 7601 | 4798 BRIARLAKE DRIVE | 404-998-2435 |
| SARAH | | MARTINS | 7598 | 3318 E WOOD VALLEY RD NW | 770-777-8716 |
| JONATHAN | | DELEO | 7600 | 4798 BRIARLAKE DRIVE | 404-998-2435 |

4 PATIENTS SUGGESTED

CREATE NEW PATIENT

CANCEL   OK

SYSTEMS AND METHODS FOR CONSOLIDATED MANAGEMENT AND DISTRIBUTION OF ORTHODONTIC CARE DATA, INCLUDING AN INTERACTIVE THREE-DIMENSIONAL TOOTH CHART MODEL

CROSS-REFERENCE TO RELATED APPLICATIONS

This application claims priority to and the benefit of U.S. Provisional Application No. 61/641,456, filed May 2, 2012, the contents of which are hereby incorporated by reference in their entirety.

BACKGROUND

1. Related Field

Various embodiments of the invention pertain to the field of orthodontic care management and more particularly to a comprehensive electronic system for managing administrative (e.g., office and practice management) and clinical (e.g., diagnosis and treatment) care data. In particular, various embodiments comprise an interactive three-dimensional tooth chart model that may be populated with a variety of elements, manipulated to simulate various perspectives and treatment impacts, interfaced with any of a variety of care or practice management data, and/or embedded within patient reports and correspondence.

2. Related Art

Providing quality and efficient medical care requires an effective medical practice management system. Practice management systems have generally encompassed at least the storage, retrieval, analysis, and transmittal of patient records, as well as the scheduling and billing for associated appointments, diagnoses, and treatments. While some practice management systems provide such practice management capabilities in a consolidated, even electronic form, traditionally many of these functions have been performed by separate systems and/or entities, thus introducing inefficiency and potential inaccuracy into the provided medical care.

Still further, even where consolidated or electronic form practice management systems are provided, the communication of diagnosis and treatment data remains less than ideal. For example, consider that the key to treatment and quality results in the field of orthodontics is the proper placement and manipulation of a variety of elements (e.g., brackets, elastics, arch-wires, and the like) upon a patient's teeth. Time consuming options include taking plaster models of a patient's upper and lower jaws and using the same to create realistic physical and/or digital models of teeth upon which a treatment plan is first applied, for subsequent transfer to the patient's actual teeth. Oftentimes, such options are not only time consuming, but also costly.

In such practices, treatment may be tracked and recorded on standard two-dimensional tooth charts. These standard tooth charts are not always intuitive to orthodontists and their attendant staff. Since it is important to track the treatment plan over time, it would be advantageous to provide an improved tooth model that allows orthodontists and their staff to maintain an accurate and intuitive record of the placements of various brackets, elastics, and/or arch-wires over the course of the treatment. Such a model would advantageously not only record placements from prior appointments, but also provide placements for future appointments.

The standard tooth chart is also disadvantageous when used to explain the diagnosis and treatment plan to a patient and/or the patient's parent or guardian. In particular, after leaving the orthodontist's appointment, the patient and oftentimes the patient's parent or guardian, are expected to remember the exact position of various elastics and other hardware components. Since these elastics and hardware components are often removed when the patient eats or brushes and flosses his or her teeth, it is important that the patient reapply the elastics and hardware components to the correct brackets and in the correct manner. Working from memory or using a standard tooth chart does not always result in the correct placements. As such, it would also be advantageous to provide systems and methods by which patients can more readily and accurately reapply elastics and other hardware.

BRIEF SUMMARY

Various embodiments provide a computer-implemented method for dynamically manipulating a three-dimensional virtual model representing a patient's teeth so as to facilitate visualization of an orthodontic treatment plan being applied thereto. The method comprises the steps of: rendering said three-dimensional virtual model based, at least in part, upon one or more images of a patient's teeth, said three-dimensional virtual model comprising a plurality of teeth, said plurality of teeth comprising two sets of oppositely-oriented teeth; and manipulating said three-dimensional virtual model via a translational movement in a two-dimensional computer display area and along a plane vertically oriented relative to said oppositely-oriented teeth, wherein said translational movement is configured to simultaneously impose a translational manipulation upon a first one of the two sets of oppositely oriented teeth and a rotational manipulation upon a second one of the two sets of oppositely oriented teeth, said simultaneous manipulation being configured to open said two sets of oppositely oriented teeth relative to one another so as to facilitate visualization of an orthodontic treatment plan for the patient's teeth.

Various embodiments provide a computer-implemented method for dynamically manipulating a three-dimensional virtual model representing a patient's teeth so as to facilitate visualization of an orthodontic treatment plan being applied thereto. The method comprises the steps of: rendering said three-dimensional virtual model based, at least in part, upon one or more images of a patient's teeth, said three-dimensional virtual model comprising a plurality of teeth, said plurality of teeth comprising two sets of oppositely-oriented teeth; and sequencing said three-dimensional virtual model through two or more of a plurality of points in time, wherein each of said plurality of points in time is associated with data indicative of said orthodontic treatment plan, such that said three-dimensional virtual model is manipulated based at least in part thereon during said sequencing.

Various embodiments provide a computer-implemented method for dynamically manipulating a three-dimensional virtual model representing a patient's teeth so as to facilitate visualization of an orthodontic treatment plan being applied thereto. The method comprises the steps of: rendering said three-dimensional virtual model based, at least in part, upon one or more images of a patient's teeth, said three-dimensional virtual model comprising a plurality of teeth, said plurality of teeth comprising two sets of oppositely-oriented teeth; placing one or more orthodontic hardware elements upon one or more teeth within said two sets of oppositely-oriented teeth; generating a representation of said three-dimensional virtual model, said representation comprising an illustration of said two sets of oppositely-oriented teeth and said one or more orthodontic hardware elements placed thereon; and transmitting said representation of said three-dimensional virtual model to said patient for said patient's reference between successive orthodontic appointments.

Various embodiments provide a non-transitory computer program product comprising at least one computer-readable storage medium having computer-readable program code portions embodied therein, the computer-readable program code portions comprising: (A) a first executable portion configured for rendering a three-dimensional virtual model based, at least in part, upon one or more images of a patient's teeth, the three-dimensional virtual model comprising a plurality of teeth, the plurality of teeth comprising two sets of oppositely-oriented teeth; and (B) a second executable portion configured for manipulating the three-dimensional virtual model, wherein: the manipulation is imposed in response to one or more movements in a two-dimensional computer display area representing a projection of the three-dimensional virtual model; and the one or more movements comprise at least translational movement in a vertical plane relative to the plurality of upper and lower teeth, the translational movement being configured to simultaneously impose a translational manipulation upon a first one of the two sets of oppositely oriented teeth and a rotational manipulation upon a second one of the two sets of oppositely oriented teeth, the simultaneous manipulation being configured to open the two sets of oppositely oriented teeth relative to one another so as to facilitate visualization of an orthodontic treatment plan for the patient's teeth.

In certain embodiments of the above described non-transitory computer program product, the two sets of oppositely-oriented teeth comprise a set of top teeth and a set of lower teeth; the translational movement in a vertical plane is in a first direction, the first direction being oriented toward the set of top teeth; and the translational movement in the first direction imposes the translational manipulation upon the set of top teeth and the rotational manipulation upon the lower teeth.

In certain embodiments of the above described non-transitory computer program product, the two sets of oppositely-oriented teeth comprise a set of top teeth and a set of lower teeth; the translational movement in a vertical plane is in a second direction, the second direction being oriented toward the set of bottom teeth; and the translational movement in the second direction imposes the rotational manipulation upon the set of top teeth and the translational manipulation upon the lower teeth.

In certain embodiments of the above described non-transitory computer program product, the second executable portion is further configured for expanding at least a portion of one of the two sets of oppositely oriented teeth outwardly relative to the other of the two sets of oppositely oriented teeth, the outward expanding occurring in a direction substantially perpendicular to the translational and rotational manipulations imposed upon the two sets of oppositely oriented teeth.

In certain embodiments of the above described non-transitory computer program product, the two sets of oppositely-oriented teeth comprise a set of top teeth and a set of lower teeth and the outward expanding is of a back portion of the set of top teeth.

In certain embodiments of the above described non-transitory computer program product, the two sets of oppositely-oriented teeth comprise a set of top teeth and a set of lower teeth and the outward expanding is of a back portion of the set of bottom teeth.

In certain embodiments of the above described non-transitory computer program product, the second executable portion is further configured for at least temporarily suspending the translational and rotational manipulations imposed upon the three-dimensional virtual model when the one or more movements in the two-dimensional computer display area travel through a location substantially intermediate the two sets of oppositely-oriented teeth.

In certain embodiments of the above described non-transitory computer program product, the second executable portion is further configured for automatically closing the two sets of oppositely-oriented teeth when the one or more movements in the two-dimensional computer display area pause for a period of time within a location substantially intermediate the two sets of oppositely-oriented teeth.

Various embodiments of the above described non-transitory computer program product further comprise a third executable portion configured for placing one or more orthodontic hardware elements upon one or more teeth within the two sets of oppositely-oriented teeth.

In certain embodiments of the above described non-transitory computer program product, the third executable portion is further configured for, subsequent to placing at least one orthodontic hardware element upon at least one tooth within the two sets of oppositely-oriented teeth, placing the same the orthodontic hardware element upon at least one additional tooth selected within a predetermined time period from the initial placement.

In certain embodiments of the above described non-transitory computer program product, the predetermined time period is approximately 1.5 seconds.

In certain embodiments of the above described non-transitory computer program product, the one or more orthodontic hardware elements are selected from the group consisting of: brackets, elastics, arch-wires, retainers, expansion appliances, and trans-palatal bars.

In certain embodiments of the above described non-transitory computer program product, the one or more orthodontic hardware elements comprise one or more elastics and the third executable portion is further configured for manipulating the visualization of the one or more elastics relative to the two sets of oppositely-oriented teeth, such that during the translational and rotational manipulations thereof, no portion of the one or more elastics travels through an interior portion of the teeth.

In certain embodiments of the above described non-transitory computer program product, the one or more elastics do not travel through the interior portions of the teeth due at least in part to one or more portions of the one or more elastics being configured to automatically sequentially snap to sequentially positioned discrete points along the teeth.

In certain embodiments of the above described non-transitory computer program product, the one or more orthodontic hardware elements comprise one or more elastics and the third executable portion is further configured for placing the one or more elastics relative to two or more teeth within the two sets of oppositely-oriented teeth, such that the one or more elastics are strung between the two or more teeth in a predetermined configuration.

In certain embodiments of the above described non-transitory computer program product, data associated with the orthodontic treatment plan is operatively associated with the three-dimensional virtual model and the non-transitory computer program product further comprises a fourth executable portion configured for generating a time-lapse visualization of the patient's teeth and one or more movements imposed thereon based at least upon an impact generated by one or more orthodontic hardware elements placed thereon during the orthodontic treatment plan.

Various embodiments of the above described non-transitory computer program product further comprise a fifth executable portion configured for generating and transmitting a representation of the three-dimensional virtual model to the patient for the patient's reference between successive orthodontic appointments.

In certain embodiments of the above described non-transitory computer program product, the three-dimensional virtual model comprises one or more elastics strung between one or more of the plurality of teeth, such that the representation is configured to assist the patient with subsequent maintenance of the one or more elastics between successive orthodontic appointments.

Various embodiments provide a non-transitory computer program product comprising at least one computer-readable storage medium having computer-readable program code portions embodied therein, the computer-readable program code portions comprising: (A) a first executable portion configured for rendering the three-dimensional virtual model based, at least in part, upon one or more images of a patient's teeth, the three-dimensional virtual model comprising a plurality of teeth, the plurality of teeth comprising two sets of oppositely-oriented teeth; and (B) a second executable portion configured for sequencing the three-dimensional virtual model through two or more of a plurality of points in time, wherein each of the plurality of points in time is associated with data indicative of the orthodontic treatment plan, such that the three-dimensional virtual model is manipulated based at least in part thereon during the sequencing.

In certain embodiments of the above described non-transitory computer program product, at least a portion of the plurality of points in time are historical relative to a current time so as to represent a previously executed orthodontic treatment plan.

In certain embodiments of the above described non-transitory computer program product, at least a portion of the plurality of points in time are historical relative to a current time, at least a portion of the plurality of points in time are futuristic relative to the current time, such that during the sequencing, the one or more images of the patient's teeth are sequenced through the plurality of historical points in time and the three-dimensional virtual model is sequenced through the plurality of futuristic points in time.

In certain embodiments of the above described non-transitory computer program product, the second executable portion is configured such that the sequencing occurs automatically across successive points in time so as to generate a time-lapse visualization of the progress of the orthodontic treatment plan.

In certain embodiments of the above described non-transitory computer program product, the second executable portion is configured such that the time-lapse visualization illustrates placement of one or more orthodontic hardware elements upon one or more teeth within the two sets of oppositely-oriented teeth and the sequencing step illustrates movement imposed upon the one or more teeth at least in part by the one or more orthodontic hardware elements over time.

In certain embodiments of the above described non-transitory computer program product, the one or more orthodontic hardware elements are selected from the group consisting of: brackets, elastics, arch-wires, retainers, expansion appliances, and trans-palatal bars.

In certain embodiments of the above described non-transitory computer program product, a third executable portion is configured for selectively pausing the sequencing and manipulating the three-dimensional virtual model via a translational movement a plane vertically oriented relative to the oppositely-oriented teeth, such that a translational manipulation is imposed upon a first one of the two sets of oppositely oriented teeth substantially simultaneously as a rotational manipulation is imposed upon a second one of the two sets of oppositely oriented teeth.

Various embodiments provide a non-transitory computer program product comprising at least one computer-readable storage medium having computer-readable program code portions embodied therein, the computer-readable program code portions comprising: (A) a first executable portion configured for rendering the three-dimensional virtual model based, at least in part, upon one or more images of a patient's teeth, the three-dimensional virtual model comprising a plurality of teeth, the plurality of teeth comprising two sets of oppositely-oriented teeth; (B) a second executable portion configured for placing one or more orthodontic hardware elements upon one or more teeth within the two sets of oppositely-oriented teeth; (C) a third executable portion configured for generating a representation of the three-dimensional virtual model, the representation comprising an illustration of the two sets of oppositely-oriented teeth and the one or more orthodontic hardware elements placed thereon; and (D) a fourth executable portion configured for transmitting the representation of the three-dimensional virtual model to the patient for the patient's reference between successive orthodontic appointments.

In certain embodiments of the above described non-transitory computer program product, the one or more hardware elements comprise one or more elastics and the representation of the three-dimensional virtual model further comprises textual instructions for patient placement of the one or more elastics alongside the visualization of the placement of the one or more elastics in the three-dimensional virtual model.

In certain embodiments of the above described non-transitory computer program product, a fifth executable portion is configured for manipulating the three-dimensional virtual model and capturing two or more screen shots of the three-dimensional virtual model from two or more angles, embedding the at least the two or more screen shots of the three-dimensional virtual model within the representation.

In certain embodiments of the above described non-transitory computer program product, the two or more screen shots comprise a left facing screen shot, a front facing screen shot, and a right facing screen shot relative to the two sets of oppositely oriented teeth.

In certain embodiments of the above described non-transitory computer program product, the representation is electronically transmitted to at least the patient.

Various embodiments provide an orthodontic care system for dynamically manipulating a three-dimensional virtual model representing a patient's teeth so as to facilitate visualization of an orthodontic treatment plan being applied thereto, the system comprising: one or more memory storage areas containing data associated with the orthodontic treatment plan; and one or more computer processors configured for: rendering a three-dimensional virtual model based, at least in part, upon one or more images of a patient's teeth, the three-dimensional virtual model comprising a plurality of teeth, the plurality of teeth comprising two sets of oppositely-oriented teeth; and manipulating the three-dimensional virtual model, wherein: the manipulation is imposed in response to one or more movements in a two-dimensional computer display area representing a projection of the three-dimensional virtual model; and the one or more movements comprise at least translational movement in a vertical plane relative to the plurality of upper and lower teeth, the translational movement being configured to simultaneously impose a translational manipulation upon a first one of the two sets of oppositely oriented teeth and a rotational manipulation upon a second one of the two sets of oppositely oriented teeth, the simultaneous manipulation being configured to open the two sets of oppositely oriented teeth relative to one another so as to facilitate visualization of an orthodontic treatment plan for the patient's teeth.

In certain embodiments of the above described system, the two sets of oppositely-oriented teeth comprise a set of top teeth and a set of lower teeth; the translational movement in a vertical plane is in a first direction, the first direction being oriented toward the set of top teeth; and the translational movement in the first direction imposes the translational manipulation upon the set of top teeth and the rotational manipulation upon the lower teeth.

In certain embodiments of the above described system, the two sets of oppositely-oriented teeth comprise a set of top teeth and a set of lower teeth; the translational movement in a vertical plane is in a second direction, the second direction being oriented toward the set of bottom teeth; and the translational movement in the second direction imposes the rotational manipulation upon the set of top teeth and the translational manipulation upon the lower teeth.

In certain embodiments of the above described system, the one or more computer processors are further configured for expanding at least a portion of one of the two sets of oppositely oriented teeth outwardly relative to the other of the two sets of oppositely oriented teeth, the outward expanding occurring in a direction substantially perpendicular to the translational and rotational manipulations imposed upon the two sets of oppositely oriented teeth.

In certain embodiments of the above described system, the two sets of oppositely-oriented teeth comprise a set of top teeth and a set of lower teeth and the outward expanding is of a back portion of the set of top teeth.

In certain embodiments of the above described system, the two sets of oppositely-oriented teeth comprise a set of top teeth and a set of lower teeth and the outward expanding is of a back portion of the set of bottom teeth.

In certain embodiments of the above described system, the one or more computer processors are further configured for at least temporarily suspending the translational and rotational manipulations imposed upon the three-dimensional virtual model when the one or more movements in the two-dimensional computer display area travel through a location substantially intermediate the two sets of oppositely-oriented teeth.

In certain embodiments of the above described system, the one or more computer processors are further configured for automatically closing the two sets of oppositely-oriented teeth when the one or more movements in the two-dimensional computer display area pause for a period of time within a location substantially intermediate the two sets of oppositely-oriented teeth.

In certain embodiments of the above described system, the one or more computer processors are further configured for placing one or more orthodontic hardware elements upon one or more teeth within the two sets of oppositely-oriented teeth.

In certain embodiments of the above described system, the one or more computer processors are further configured for, subsequent to placing at least one orthodontic hardware element upon at least one tooth within the two sets of oppositely-oriented teeth, placing the same the orthodontic hardware element upon at least one additional tooth selected within a predetermined time period from the initial placement.

In certain embodiments of the above described system, the predetermined time period is approximately 1.5 seconds.

In certain embodiments of the above described system, the one or more orthodontic hardware elements are selected from the group consisting of: brackets, elastics, arch-wires, retainers, expansion appliances, and trans-palatal bars.

In certain embodiments of the above described system, the one or more orthodontic hardware elements comprise one or more elastics and the third executable portion is further configured for manipulating the visualization of the one or more elastics relative to the two sets of oppositely-oriented teeth, such that during the translational and rotational manipulations thereof, no portion of the one or more elastics travels through an interior portion of the teeth.

In certain embodiments of the above described system, the one or more elastics do not travel through the interior portions of the teeth due at least in part to one or more portions of the one or more elastics being configured to automatically sequentially snap to sequentially positioned discrete points along the teeth.

In certain embodiments of the above described system, the one or more orthodontic hardware elements comprise one or more elastics and the third executable portion is further configured for placing the one or more elastics relative to two or more teeth within the two sets of oppositely-oriented teeth, such that the one or more elastics are strung between the two or more teeth in a predetermined configuration.

In certain embodiments of the above described system, data associated with the orthodontic treatment plan is operatively associated with the three-dimensional virtual model and the one or more computer processors are further configured for generating a time-lapse visualization of the patient's teeth and one or more movements imposed thereon based at least upon an impact generated by one or more orthodontic hardware elements placed thereon during the orthodontic treatment plan.

In certain embodiments of the above described system, the one or more computer processors are further configured for generating and transmitting a representation of the three-dimensional virtual model to the patient for the patient's reference between successive orthodontic appointments.

In certain embodiments of the above described system, the three-dimensional virtual model comprises one or more elastics strung between one or more of the plurality of teeth, such that the representation is configured to assist the patient with subsequent maintenance of the one or more elastics between successive orthodontic appointments.

Various embodiments provide an orthodontic care system for dynamically manipulating a three-dimensional virtual model representing a patient's teeth so as to facilitate visualization of an orthodontic treatment plan being applied thereto, the system comprising: one or more memory storage areas containing data associated with the orthodontic treatment plan; and one or more computer processors configured for: rendering the three-dimensional virtual model based, at least in part, upon one or more images of a patient's teeth, the three-dimensional virtual model comprising a plurality of teeth, the plurality of teeth comprising two sets of oppositely-oriented teeth; and sequencing the three-dimensional virtual model through two or more of a plurality of points in time, wherein each of the plurality of points in time is associated with data indicative of the orthodontic treatment plan, such that the three-dimensional virtual model is manipulated based at least in part thereon during the sequencing.

In certain embodiments of the above described system, at least a portion of the plurality of points in time is historical relative to a current time so as to represent a previously executed orthodontic treatment plan.

In certain embodiments of the above described system, at least a portion of the plurality of points in time are historical relative to a current time, at least a portion of the plurality of points in time are futuristic relative to the current time, such that during the sequencing, the one or more images of the patient's teeth are sequenced through the plurality of historical points in time and the three-dimensional virtual model is sequenced through the plurality of futuristic points in time.

In certain embodiments of the above described system, the one or more computer processors are further configured such that the sequencing occurs automatically across successive points in time so as to generate a time-lapse visualization of the progress of the orthodontic treatment plan.

In certain embodiments of the above described system, the one or more computer processors are further configured such that the time-lapse visualization illustrates placement of one or more orthodontic hardware elements upon one or more teeth within the two sets of oppositely-oriented teeth and the sequencing step illustrates movement imposed upon the one or more teeth at least in part by the one or more orthodontic hardware elements over time.

In certain embodiments of the above described system, the one or more orthodontic hardware elements are selected from the group consisting of: brackets, elastics, arch-wires, retainers, expansion appliances, and trans-palatal bars.

In certain embodiments of the above described system, the one or more computer processors are further configured for selectively pausing the sequencing and manipulating the three-dimensional virtual model via a translational movement a plane vertically oriented relative to the oppositely-oriented teeth, such that a translational manipulation is imposed upon a first one of the two sets of oppositely oriented teeth substantially simultaneously as a rotational manipulation is imposed upon a second one of the two sets of oppositely oriented teeth.

Various embodiments provide an orthodontic care system for dynamically manipulating a three-dimensional virtual model representing a patient's teeth so as to facilitate visualization of an orthodontic treatment plan being applied thereto, the system comprising: one or more memory storage areas containing data associated with the orthodontic treatment plan; and one or more computer processors configured for: for rendering the three-dimensional virtual model based, at least in part, upon one or more images of a patient's teeth, the three-dimensional virtual model comprising a plurality of teeth, the plurality of teeth comprising two sets of oppositely-oriented teeth; placing one or more orthodontic hardware elements upon one or more teeth within the two sets of oppositely-oriented teeth; generating a representation of the three-dimensional virtual model, the representation comprising an illustration of the two sets of oppositely-oriented teeth and the one or more orthodontic hardware elements placed thereon; and transmitting the representation of the three-dimensional virtual model to the patient for the patient's reference between successive orthodontic appointments.

In certain embodiments of the above described system, the one or more hardware elements comprise one or more elastics and the representation of the three-dimensional virtual model further comprises textual instructions for patient placement of the one or more elastics alongside the visualization of the placement of the one or more elastics in the three-dimensional virtual model.

In certain embodiments of the above described system, the one or more computer processors are configured for manipulating the three-dimensional virtual model and capturing two or more screen shots of the three-dimensional virtual model from two or more angles, embedding the at least the two or more screen shots of the three-dimensional virtual model within the representation.

In certain embodiments of the above described system, the two or more screen shots comprise a left facing screen shot, a front facing screen shot, and a right facing screen shot relative to the two sets of oppositely oriented teeth.

In certain embodiments of the above described system, the representation is electronically transmitted to at least the patient.

BRIEF DESCRIPTION OF THE SEVERAL VIEWS OF THE DRAWING(S)

The accompanying drawings incorporated herein and forming a part of the disclosure illustrate several aspects of the present invention and together with the detailed description serve to explain certain principles of the present invention. In the drawings, which are not necessarily drawn to scale:

FIG. 3 is an exemplary view of a screen display 501 of a user interface of a home module 500 according to various embodiments;

Figure 5:
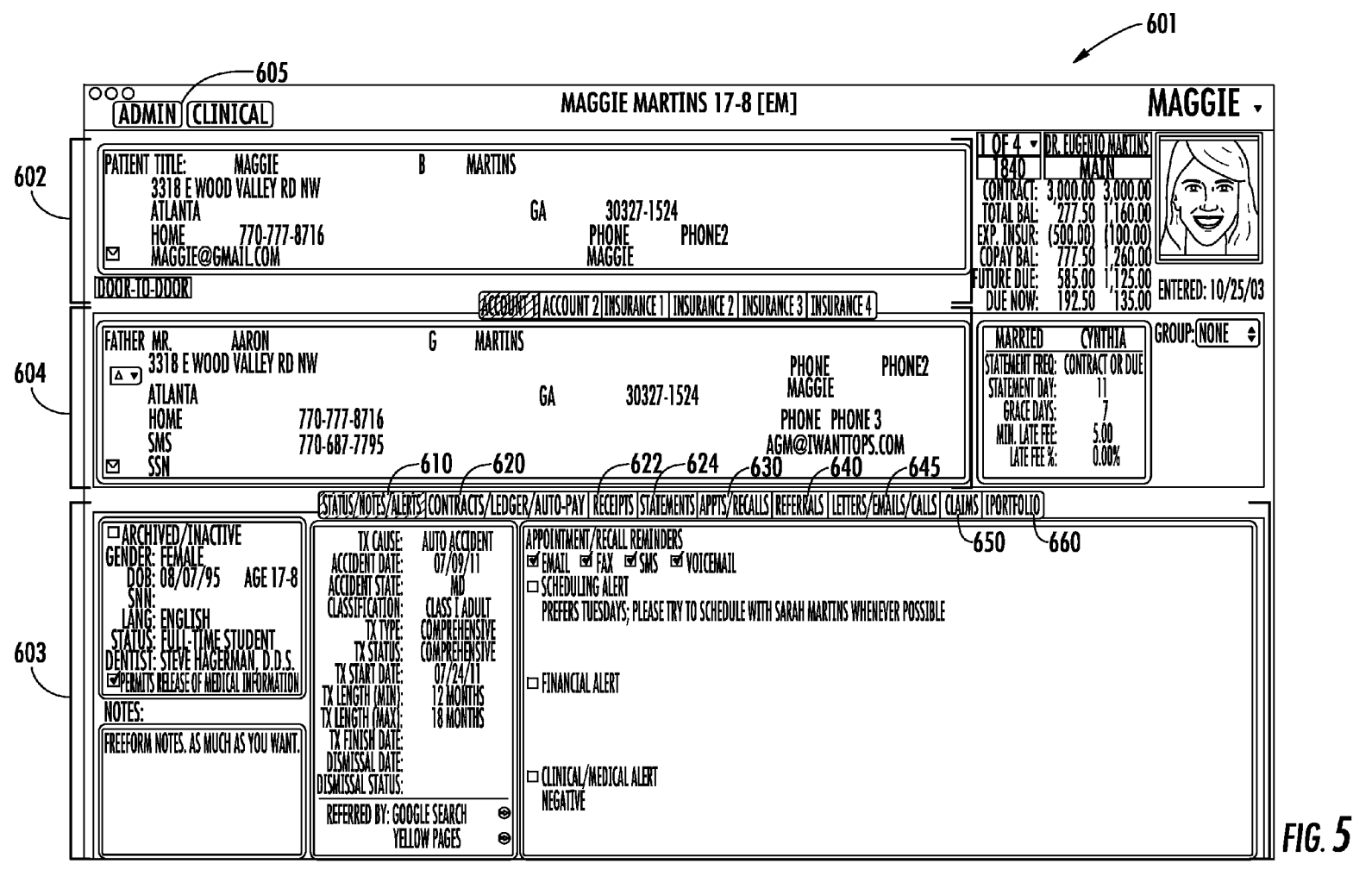
Figure 1:
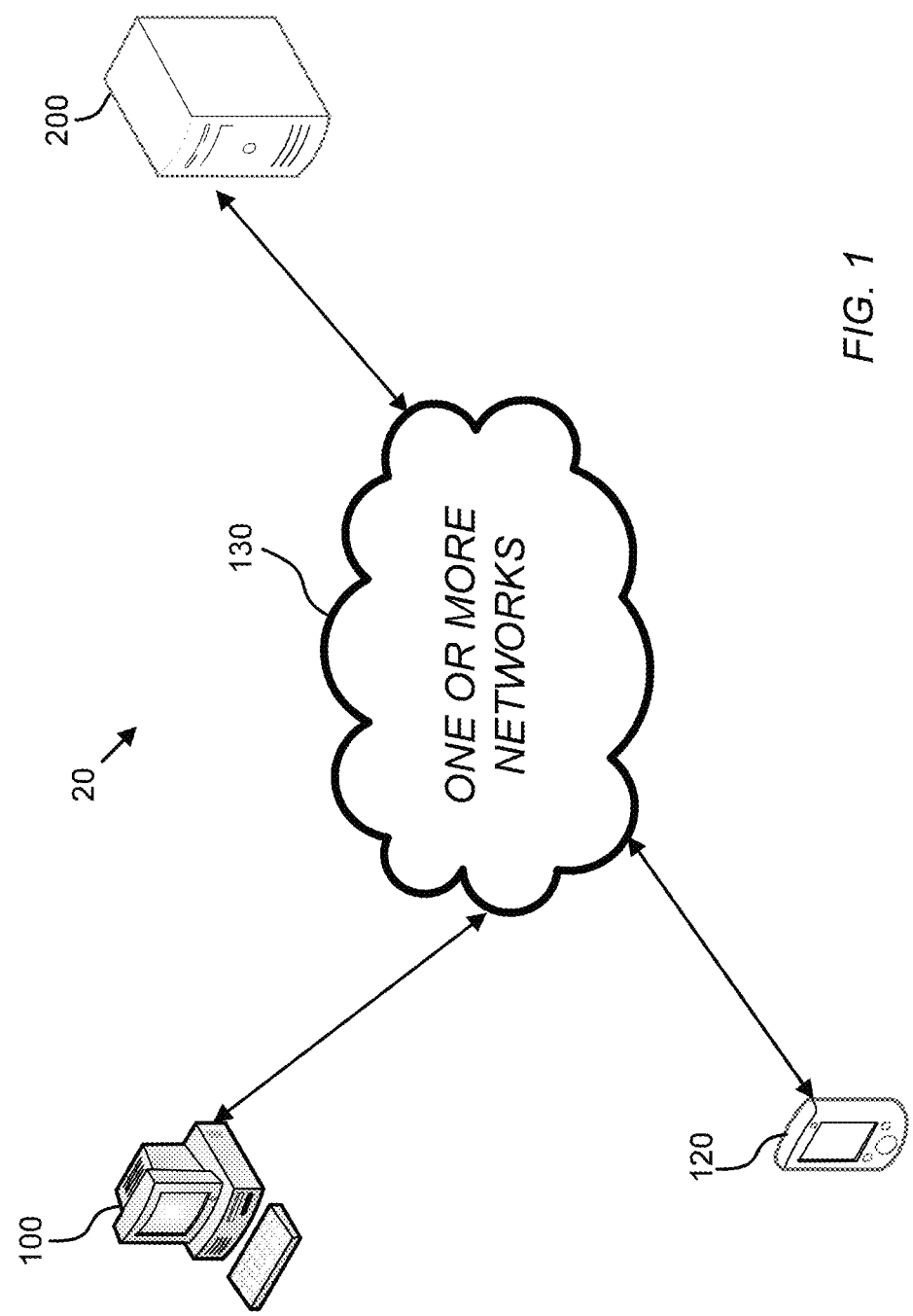
FIG. 1 is a block diagram of a orthodontic care management system 5 according to various embodiments.
Figure 15:
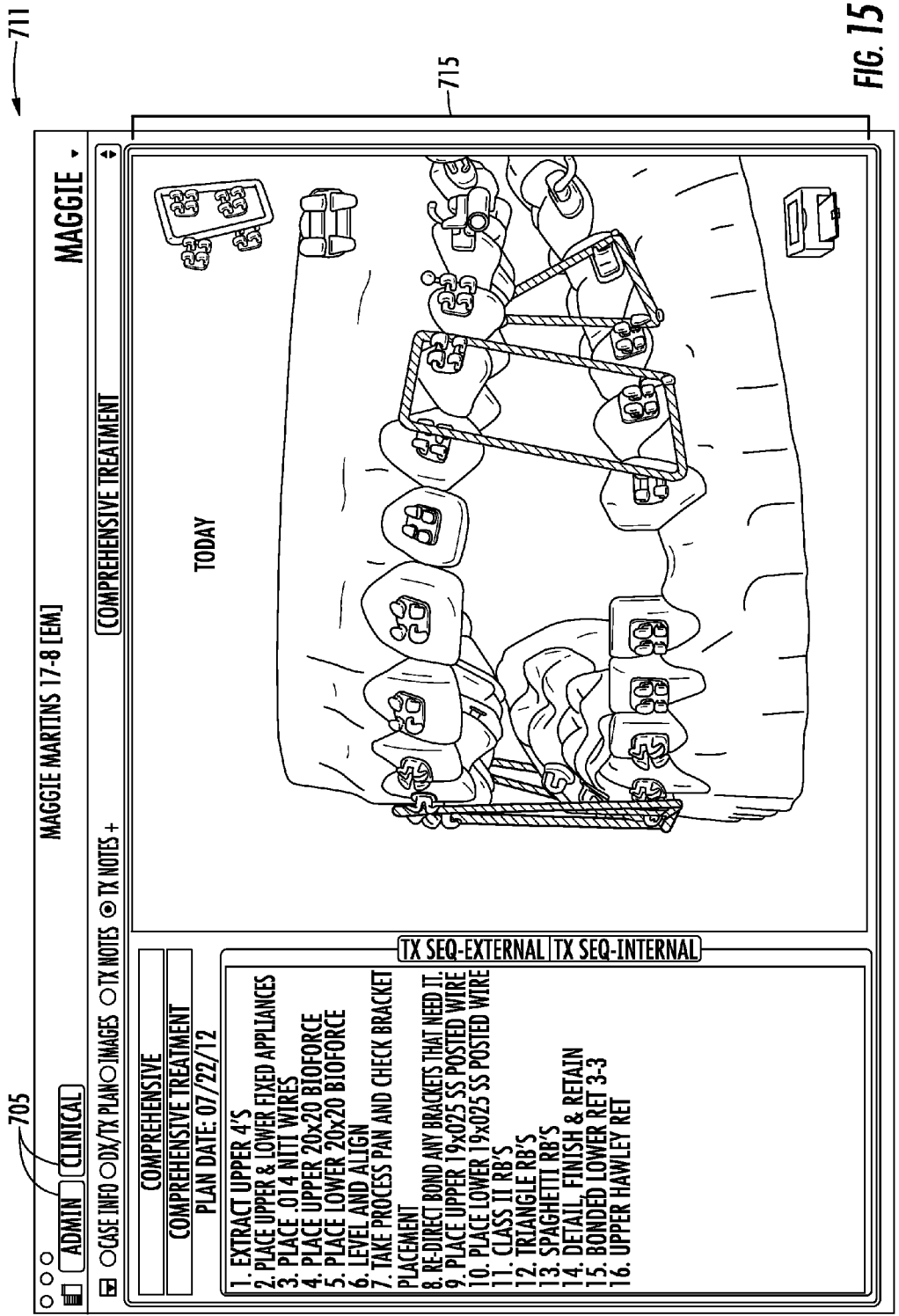
Figure 16:
Figure 17:
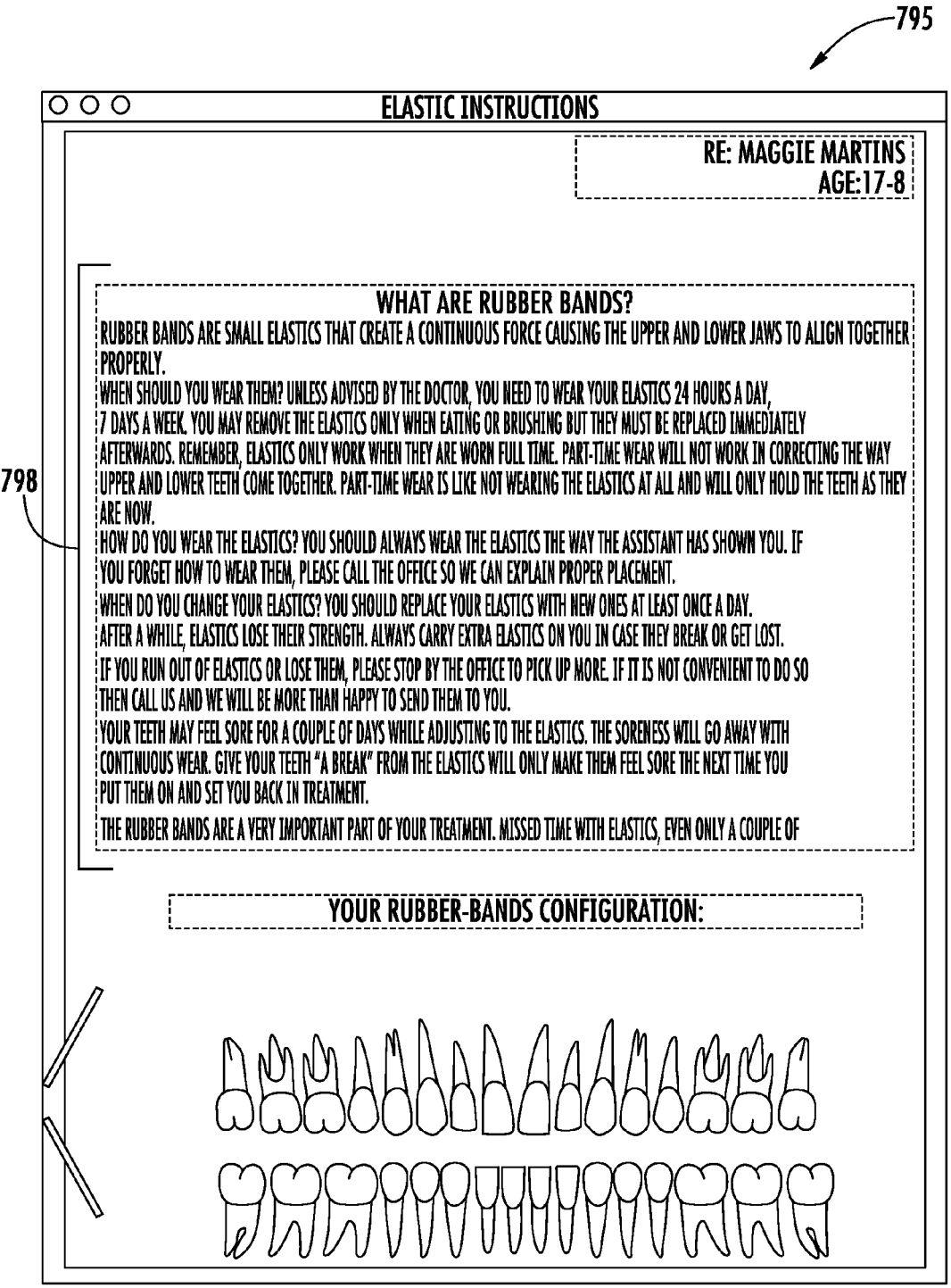
Figure 18:
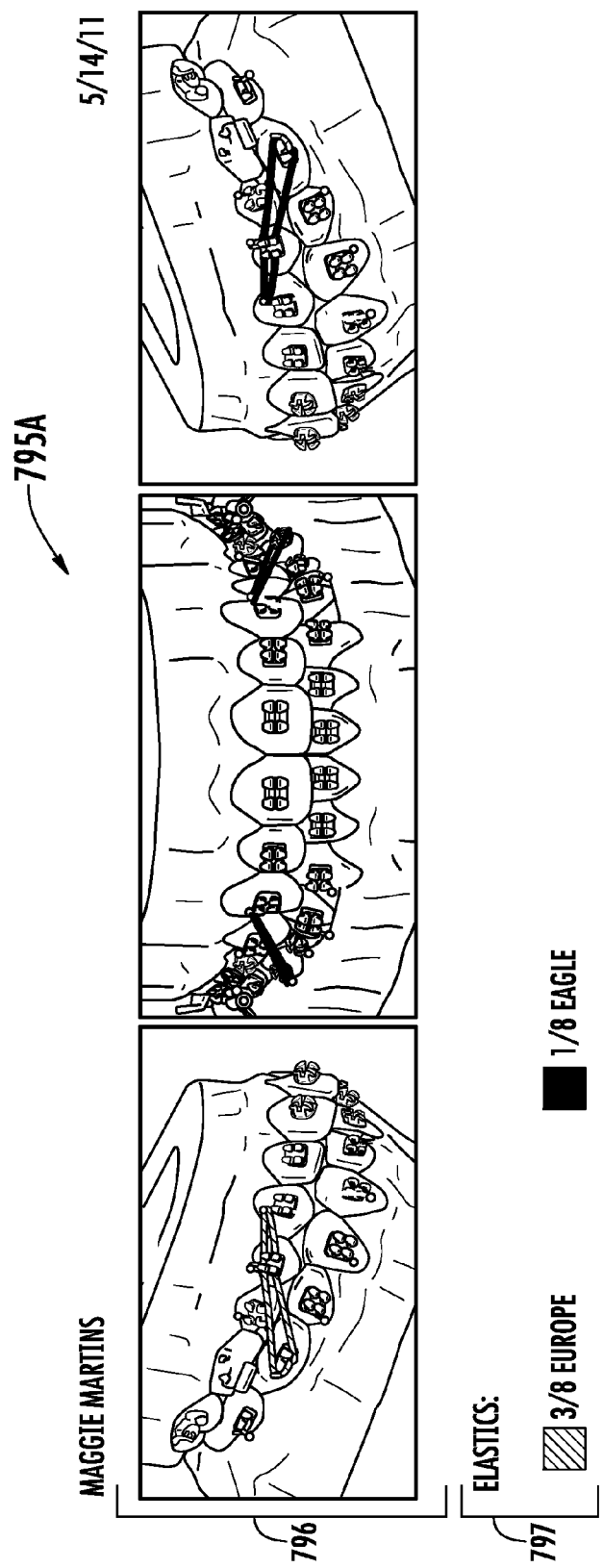
Figure 19A:
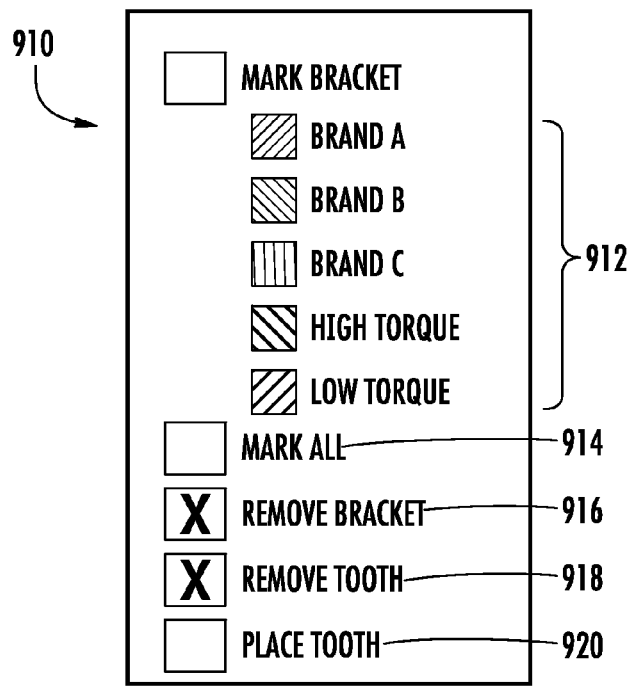
Figure 19B:
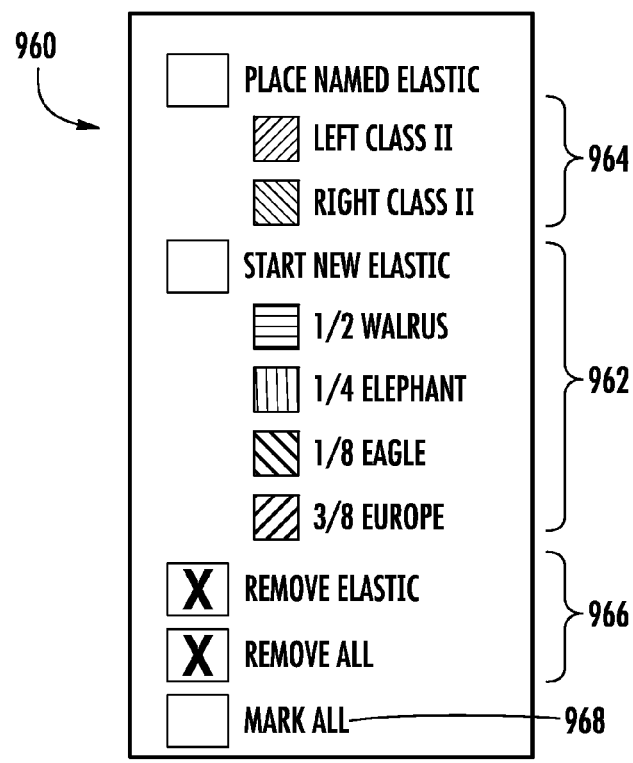

FIG. 5 is an exemplary view of a screen display 601 of a user interface of an admin module 600 according to various embodiments, further illustrating an exemplary sub-display, namely a status display 610, according to various embodiments;

Figure 6:
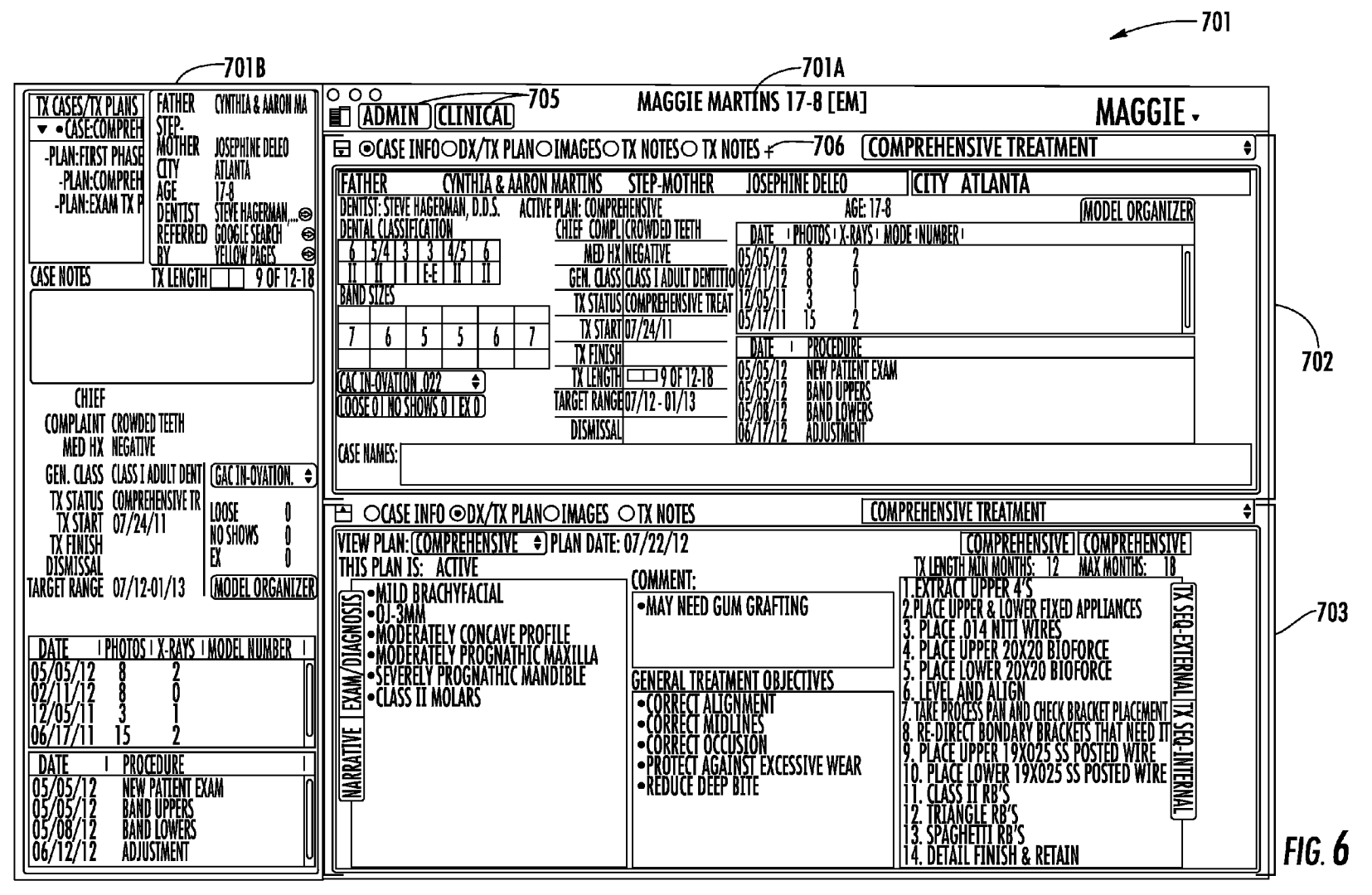

FIG. 6 is an exemplary view of a clinical display 701 of a user interface of a clinical module 700 according to various embodiments, further illustrating an overview display 702 and a care planning display 703 according to various embodiments;

Figure 7:
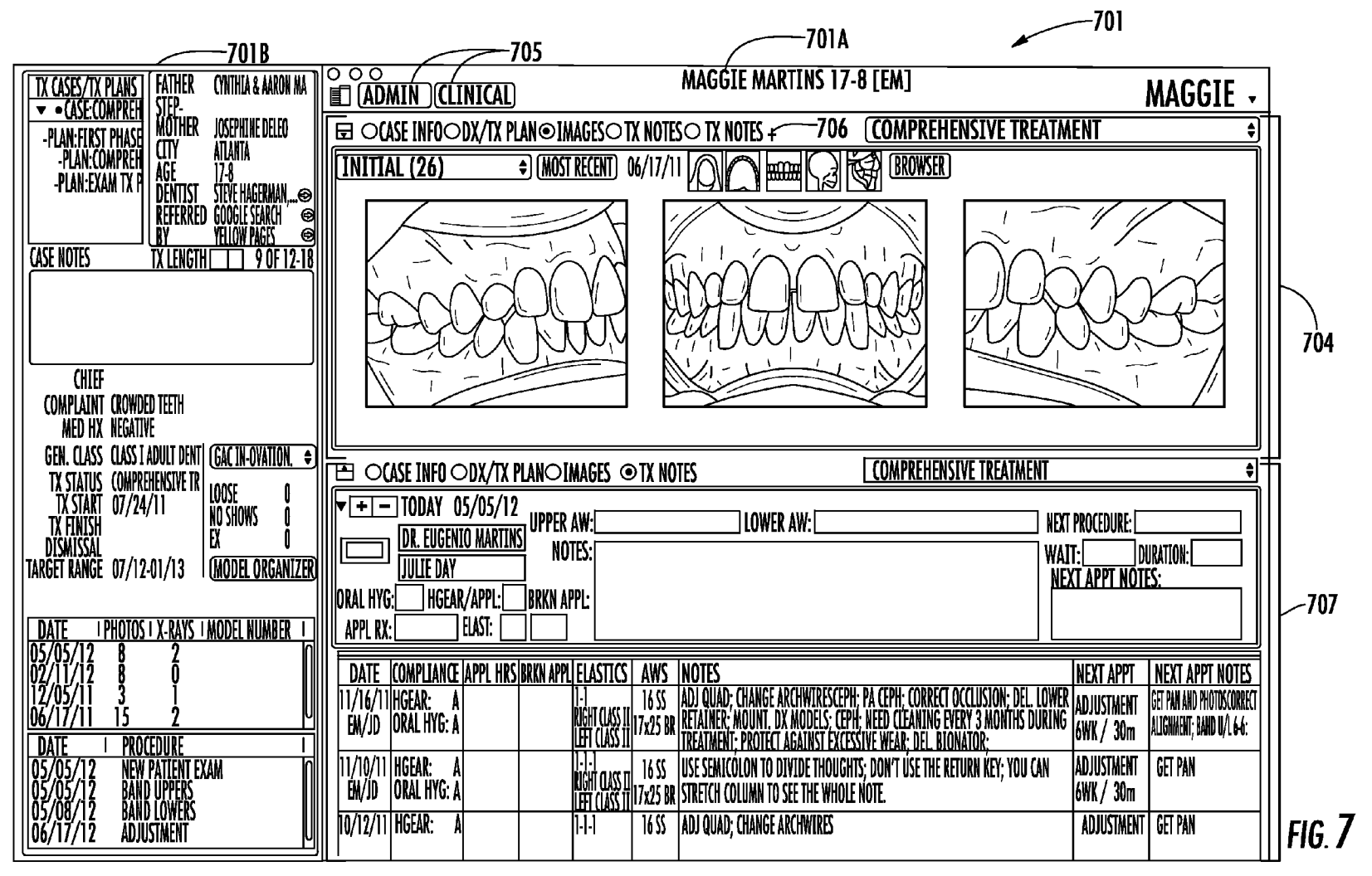

FIG. 7 is an exemplary view of the clinical display 701 of FIG. 6, further illustrating an imaging display 704 and a textual treatment display 707 according to various embodiments;

Figure 8:
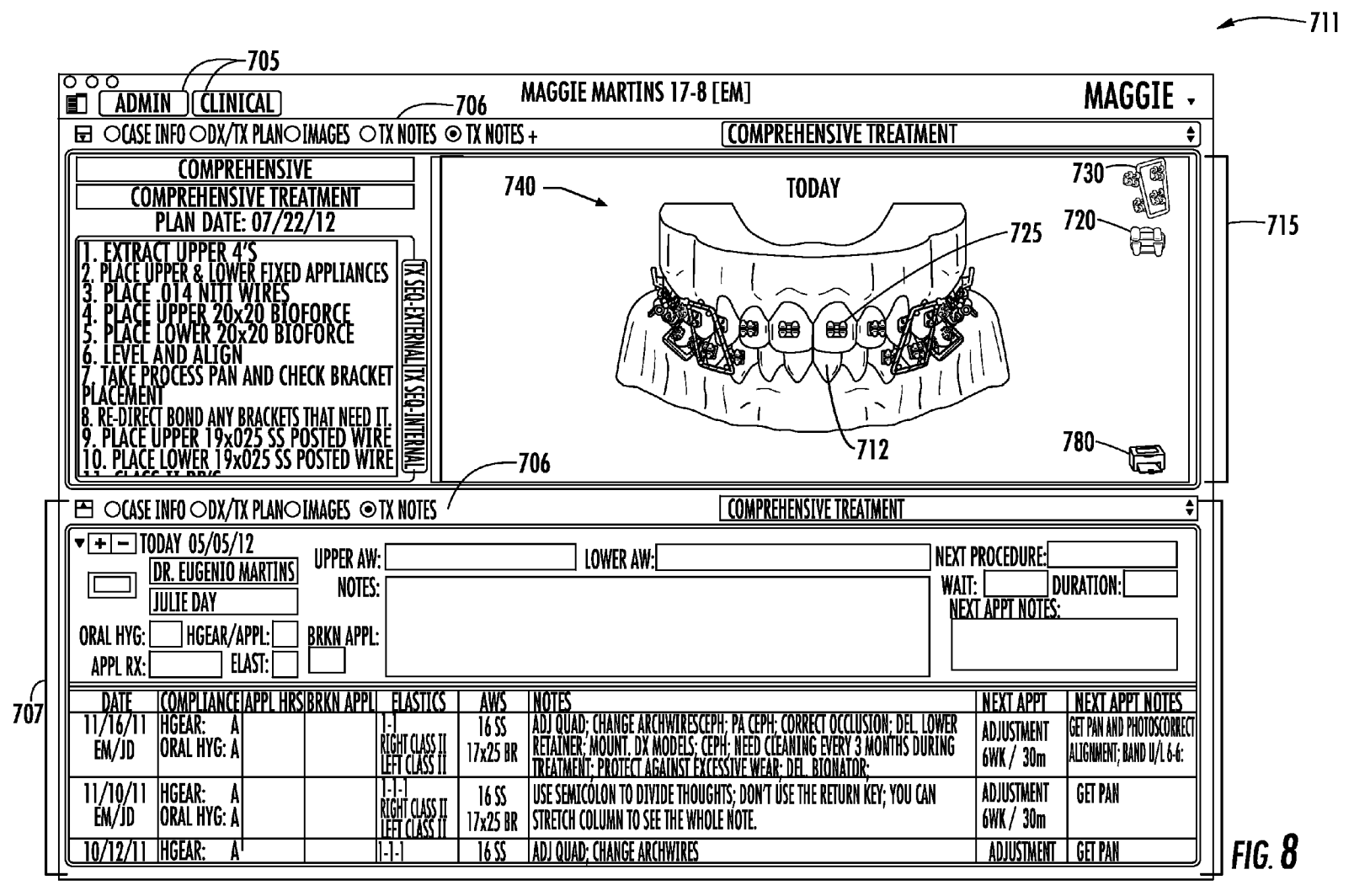

FIG. 8 is an exemplary view of the clinical display 701 of FIG. 6, further illustrating a graphical treatment display 711 according to various embodiments, the graphical treatment display 711 comprising an interactive three-dimensional tooth chart 715 having a bracket tool 720, an elastics tool 730, a report tool 780, further with the tooth chart positioned in a closed teeth configuration 740 according to various embodiments;

Figure 9:
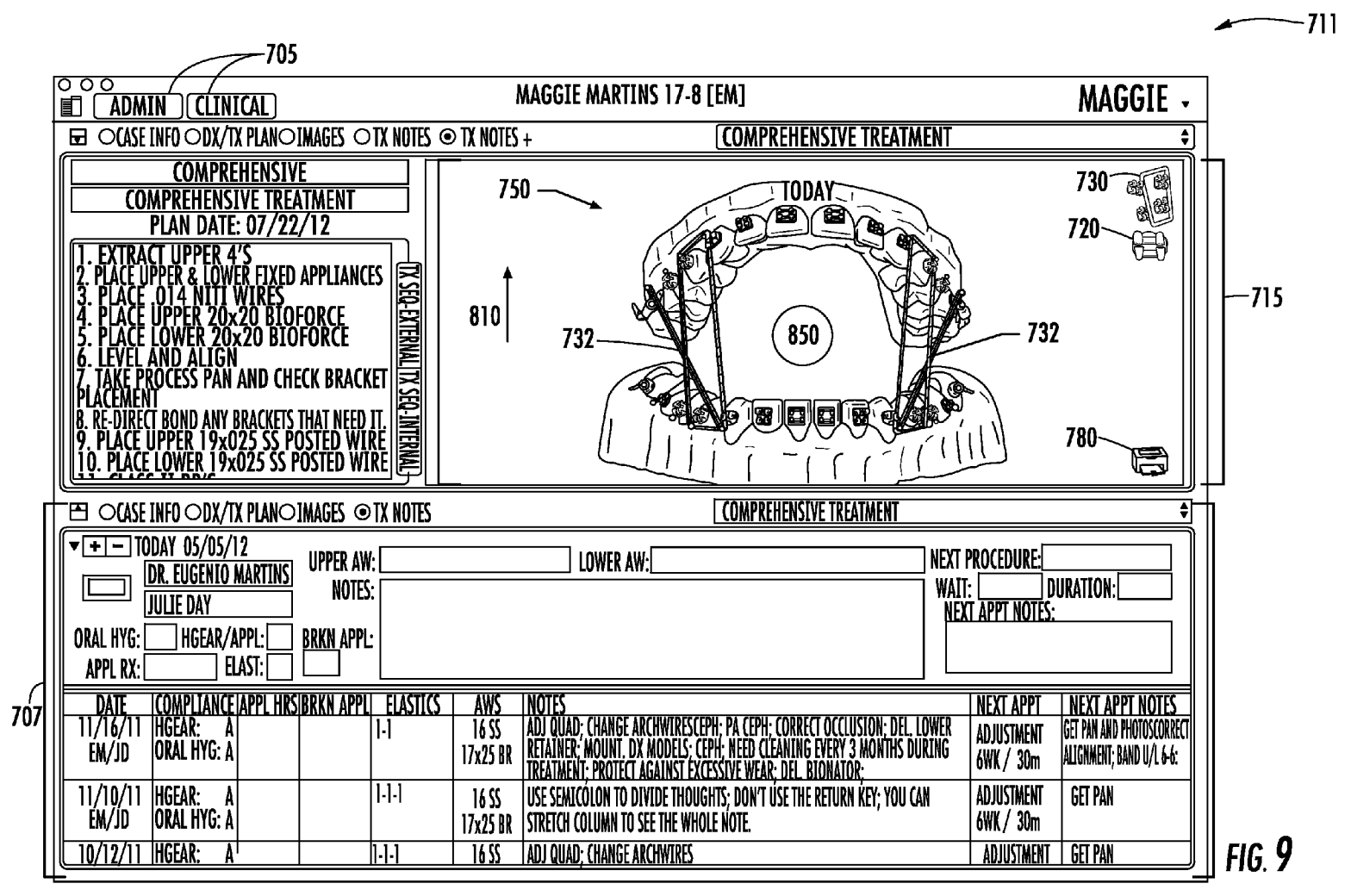

FIG. 9 is another view of the graphical treatment display 711 of FIG. 8, further illustrating a top teeth opened configuration 750 of the interactive three-dimensional tooth chart according to various embodiments;

Figure 10:
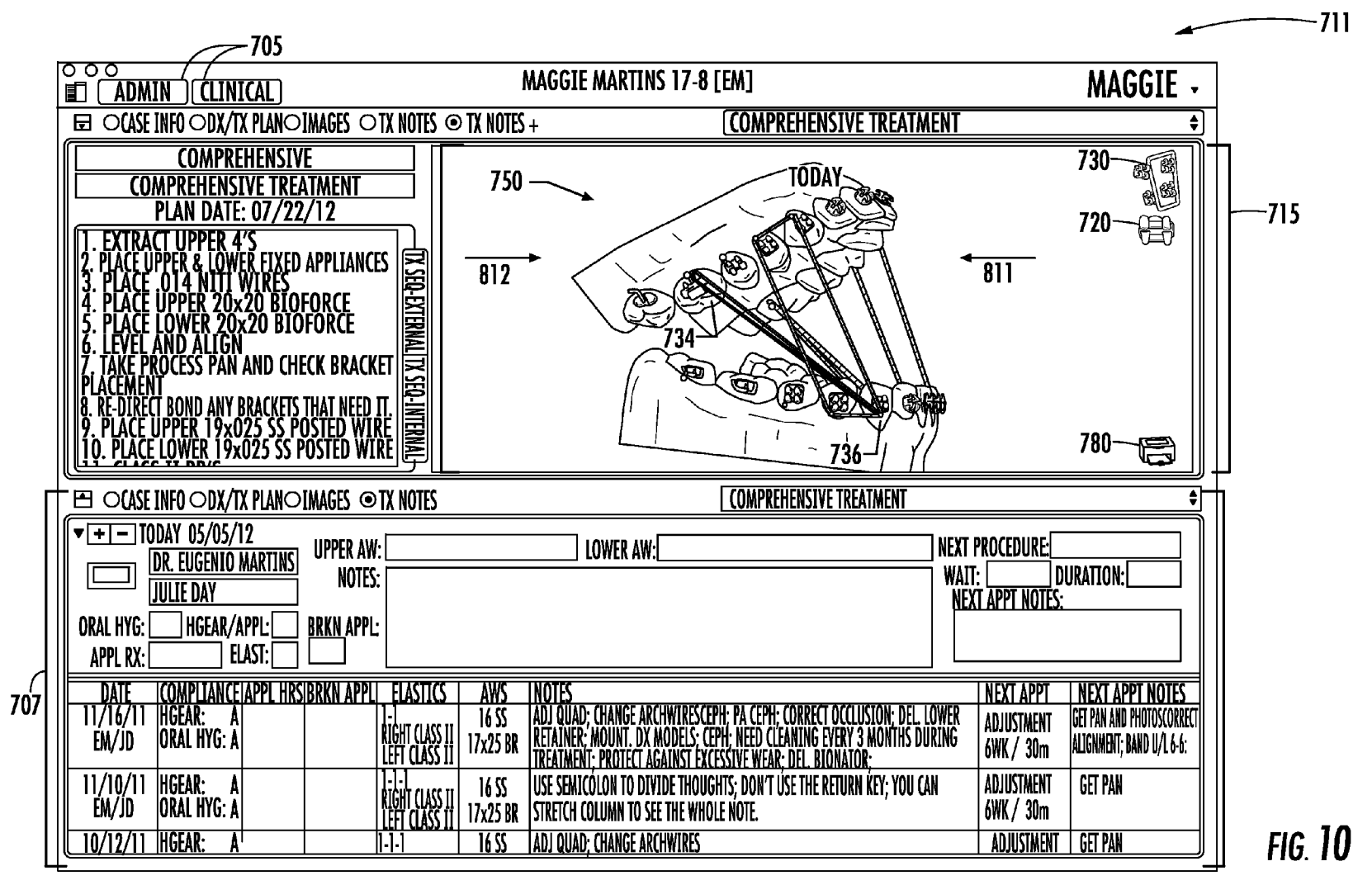

FIG. 10 is another view of the top teeth opened configuration 750 of FIG. 9 according to various embodiments, further illustrating rotational manipulations 811, 812 provided in certain embodiments;

Figure 11:
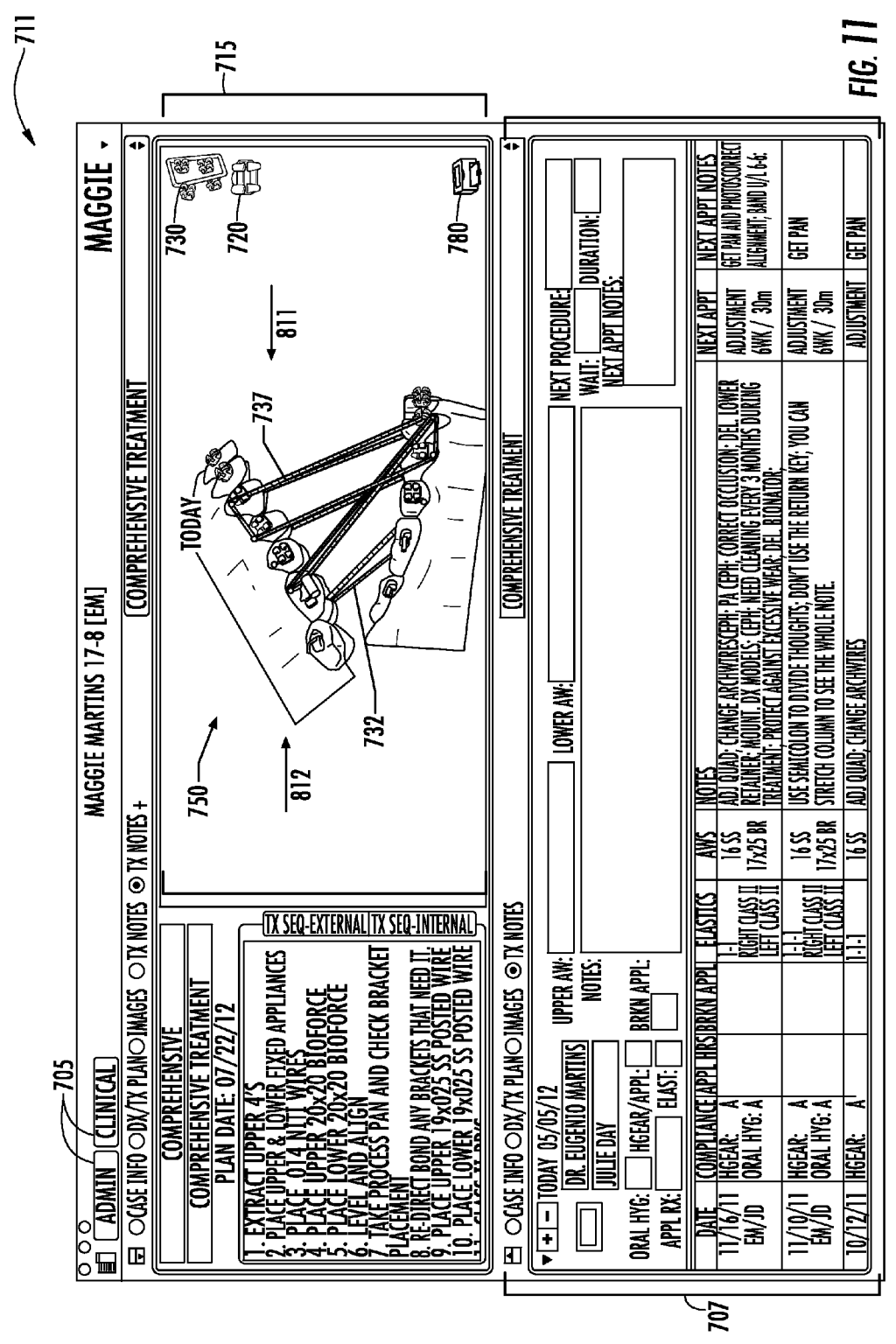

FIG. 11 is another view of the top teeth opened configuration 750 of FIG. 9 according to various embodiments, further illustrating a customized bracket configuration 737 that may be provided in certain embodiments;

Figure 12:
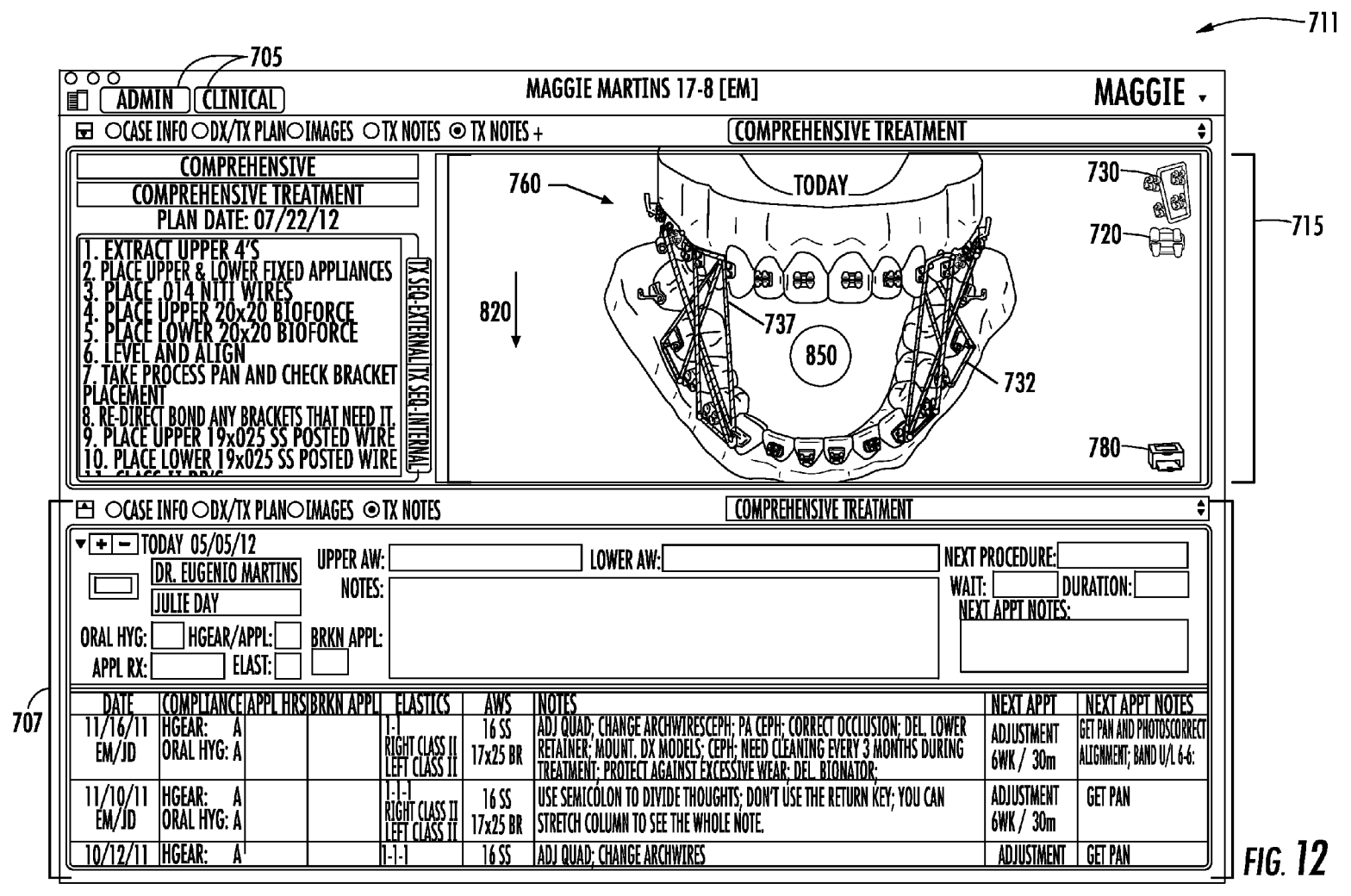

FIG. 12 is an exemplary view of the graphical treatment display 711 of FIG. 8, further illustrating a bottom teeth opened configuration 760 the interactive three-dimensional tooth chart 715 according to various embodiments;

Figure 13:
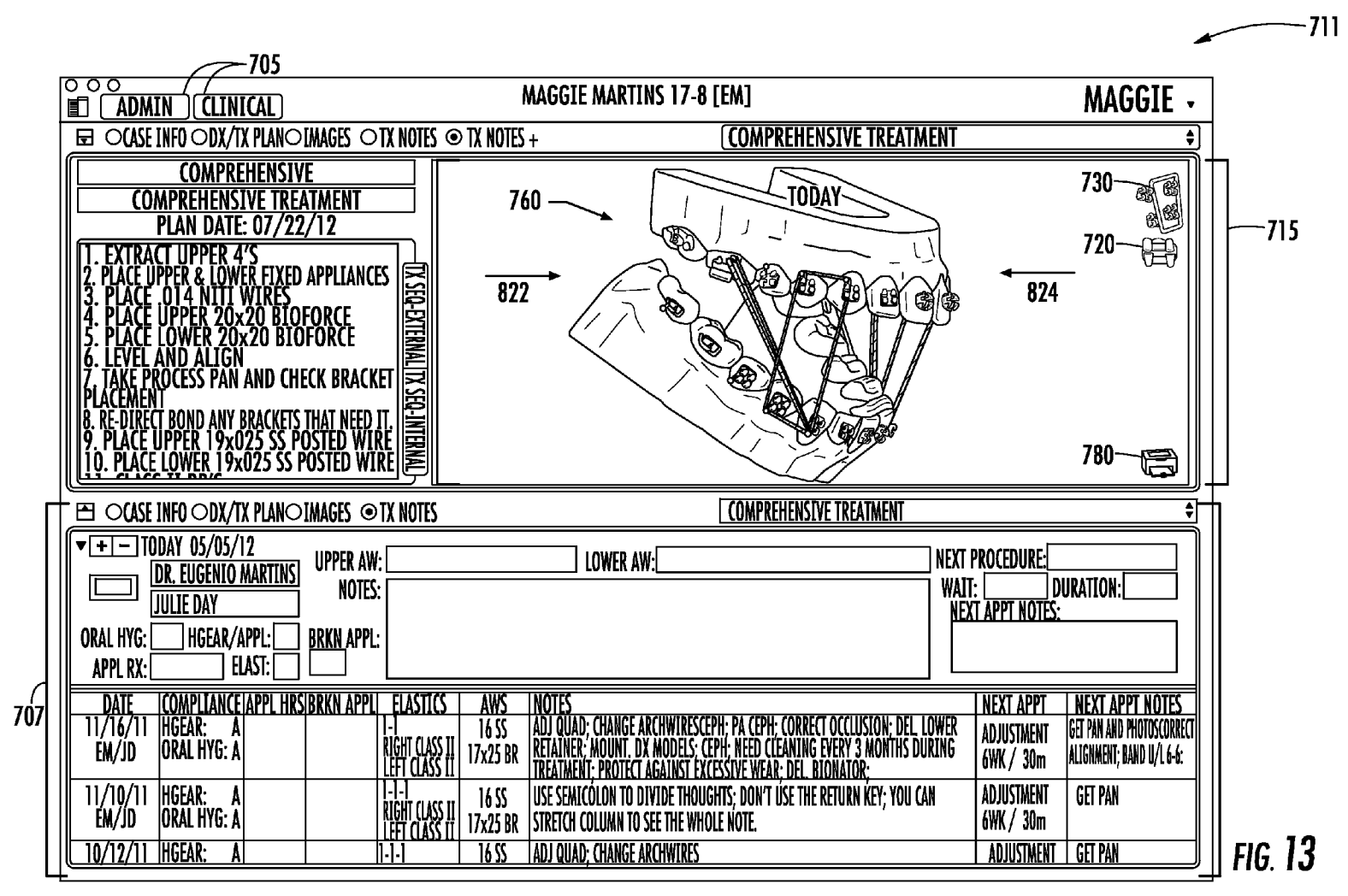

FIG. 13 is another view of the bottom teeth opened configuration 760 of FIG. 12 according to various embodiments;

Figure 14:
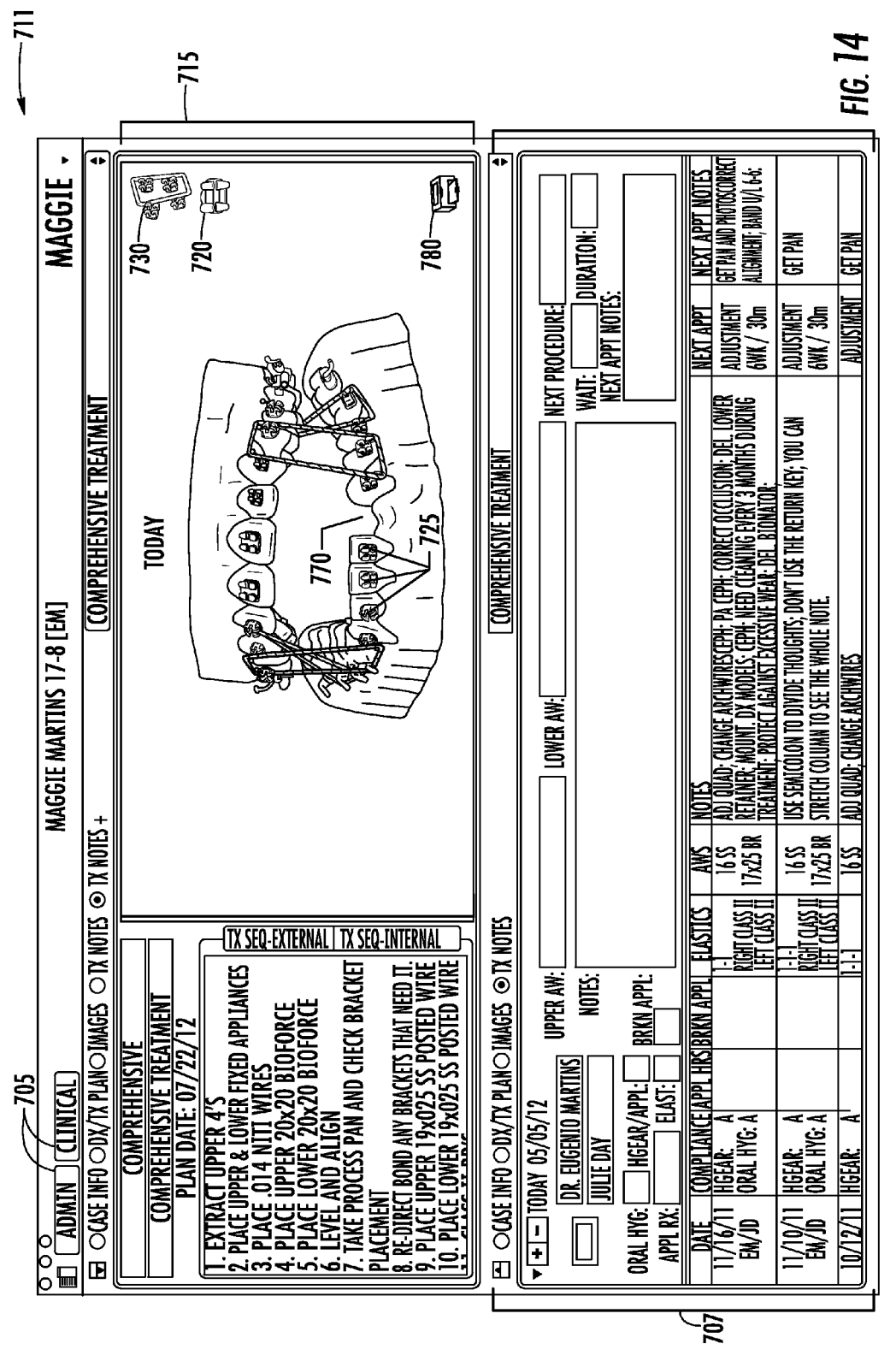

FIG. 14 is another view of the graphical treatment display 711 of FIG. 8, further illustrating at least a removed tooth 770 in the interactive three-dimensional tooth chart 715 according to various embodiments;

FIG. 15 is a view of a full screen view of the interactive three-dimensional tooth chart 715 of the graphical treatment display 711 of the clinical display 701 of FIG. 8 according to various embodiments;

FIG. 16 is a view of a report display 791 of the report module 790 executed by the report tool 780 of FIG. 15 according to various embodiments;

FIG. 17 is an exemplary view of an instructive report 795, as may be generated by the report module 790 according to various embodiments;

FIG. 18 is an exemplary view of an alternative instructive report 795A obtainable via the report module 790 according to various embodiments;

FIG. 19A is a view of a "pop-up" window 910 according to various embodiments of the bracket tool 720 of FIG. 8; and FIG. 19B is a view of a "pop-up" window 960 according to various embodiments of the elastics tool 730 of FIG. 8.

DETAILED DESCRIPTION OF VARIOUS EMBODIMENTS

Various embodiments of the present invention now will be described more fully hereinafter with reference to the accompanying drawings, in which some, but not all embodiments of the inventions are shown. Indeed, embodiments of the invention may be embodied in many different forms and should not be construed as limited to the embodiments set forth herein. Rather, these embodiments are provided so that this disclosure will satisfy applicable legal requirements. Unless otherwise defined, all technical and scientific terms used herein have the same meaning as commonly known and understood by one of ordinary skill in the art to which the invention relates. The term "or" is used herein in both the alternative and conjunctive sense, unless otherwise indicated. Like numbers refer to like elements throughout.

Apparatuses, Methods, Systems, and Computer Program Products

As should be appreciated, various embodiments may be implemented in various ways, including as apparatuses, methods, systems, or computer program products. Accordingly, the embodiments may take the form of an entirely hardware embodiment or an embodiment in which one or more processors are programmed to perform certain steps. Furthermore, various implementations may take the form of a computer program product on a computer-readable storage medium having computer-readable program instructions embodied in the storage medium. Any suitable computer-readable storage medium may be utilized including hard disks, CD-ROMs, optical storage devices, or magnetic storage devices.

Various embodiments are described below with reference to block diagrams and flowchart illustrations of methods, apparatuses, systems, and computer program products. It should be understood that each block of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions and program instructions for performing the specified functions. It should also be understood that each block of the block diagrams and flowchart illustrations, and combinations of blocks in the block diagrams and flowchart illustrations, could be implemented by special purpose hardware-based computer systems that perform the specified functions or operations, or combinations of special purpose hardware and computer instructions.

Exemplary System Architecture

FIG. 1 provides an illustration of an exemplary orthodontic care management system 5 that can be used in conjunction with various embodiments of the present invention. As shown, in FIG. 1, the system may include one or more networks 130, one or more handheld devices 120, a central server 200, and one or more distributed terminals 100. While FIG. 1 illustrates the various system entities as separate, standalone entities, it should be understood that the various embodiments are not necessarily limited to this particular architecture, as in certain embodiments, the system 5 may be located at least substantially upon a personal computing device (e.g., laptop or handheld device), as may be desirable for particular applications.

According to various embodiments of the present invention, the one or more networks 130 may be capable of supporting communication in accordance with any one or more of a number of second-generation (2G), 2.5G, third-generation (3G), and/or fourth-generation (4G) mobile communication protocols, or the like. More particularly, the one or more networks 130 may be capable of supporting communication in accordance with 2G wireless communication protocols IS-136 (TDMA), GSM, and IS-95 (CDMA). Also, for example, the one or more networks 130 may be capable of supporting communication in accordance with 2.5G wireless communication protocols GPRS, Enhanced Data GSM Environment (EDGE), or the like. In addition, for example, the one or more networks 130 may be capable of supporting communication in accordance with 3G and 4G wireless communication protocols such as Universal Mobile Telephone System (UMTS) network employing Wideband Code Division Multiple Access (WCDMA) radio access technology. Some narrow-band AMPS (NAMPS), as well as TACS, network(s) may also benefit from embodiments of the present invention, as should dual or higher mode mobile stations (e.g., digital/analog or TDMA/CDMA/analog phones). As yet another example, each of the components of the system 5 may be configured to communicate with one another in accordance with techniques such as, for example, radio frequency (RF), Bluetooth™, infrared (IrDA), or any of a number of different wired and/or wireless networking techniques, including a wired or wireless Personal Area Network ("PAN"), Local Area Network ("LAN"), Metropolitan Area Network ("MAN"), Wide Area Network ("WAN"), or the like.

Although the one or more handheld devices 120, the central server 200, and the one or more distributed terminals 100 are illustrated in FIG. 1 as communicating with one another over the same one or more networks 130, these devices may likewise communicate over multiple, separate networks. For example, while the one or more data acquisition devices 120 may communicate with the central server 200 over a wireless personal area network (WPAN) using, for example, Bluetooth techniques, the one or more distributed terminals 100 may communicate with the central server 200 over a wireless wide area network (WWAN), for example, in accordance with EDGE, or some other 2.5G wireless communication protocol. It should be understood that according to various embodiments, any of a variety of combinations of network types and/or capabilities may be employed, as may be desirable for particular applications.

According to various embodiments, in addition to receiving data from one or more of the distributed terminals 100 and/or the central server 200, the one or more handheld devices 120 may be further configured to collect and transmit data of its own. For example, according to certain embodiments, the handheld devices 120 may include a camera and/or scanner for collecting data in the form of the non-limiting examples of medical records, orthodontic images, and/or elastics configurations, all as will be described in further detail below. In particular embodiments, this camera and/or scanner may be used to gather information regarding any of a variety of items, which may then be used by one or more program modules, as will also be described in further detail below.

The one or more handheld devices 120 may be any device associated with a service provider (e.g., an orthodontic office). In various embodiments, the one or more handheld devices 120 may be capable of receiving data via one or more input units or devices, such as a keypad, touchpad, barcode scanner, radio frequency identification (RFID) reader, interface card (e.g., modem, etc.), receiver, or the like. The one or more handheld devices 120 may likewise be capable of receiving data via any of a variety of wireless networks, as previously described herein. The one or more handheld devices 120 may further be capable of storing data to one or more volatile or non-volatile memory modules, and outputting the data via one or more output units or devices, for example, by displaying data to the user operating the device, or by transmitting data, for example over the one or more networks 130. In certain embodiments, the one or more handheld devices 120 may also be capable of manipulating and/or comparing received or transmitted data, as will be described in further detail below.

The one or more distributed terminals 100, in various embodiments, may be any device capable of collecting and/or receiving data via one or more input units or devices, such as a keypad, touchpad, barcode scanner, RFID, interface card (e.g., modem, etc.), or receiver. The one or more distributed terminals 100 may likewise be capable of receiving data via any of a variety of wireless networks, as previously described herein in the context of the one or more handheld devices 120. The one or more distributed terminals 100 may further be capable of storing data to one or more volatile or non-volatile memory modules, and outputting the data via one or more output units or devices, for example, by displaying data to the user(s) operating the one or more terminals 100, or by transmitting data, for example, over the one or more networks 130. In certain embodiments, one or more of the distributed terminals 100 is associated with a user (e.g., an orthodontist or an administrative assistant thereof) remote from the central server 200 such that, for example, it is not required that the server 200 be physically located in the offices of the orthodontist using the terminals 100 or handheld devices 120, and further that the server 200 may be located at the facilities of a remote service provider. Of course, in other embodiments, it should be understood that one or more of the terminals 100, the server 200, and/or the handheld devices 120 may not be physically distributed relative to one another.

Exemplary Central Server 200 Architecture

In various embodiments, the central server 200 includes various systems for performing one or more functions in accordance with embodiments of the present invention, including those more particularly shown and described herein. It should be understood, however, that the server 200 might include a variety of alternative devices for performing one or more like functions, without departing from the spirit and scope of the present invention. For example, at least a portion of the server 200, in certain embodiments, may be located on the one or more handheld devices 120 and/or the one or more distributed terminals 100.

Figure 2:
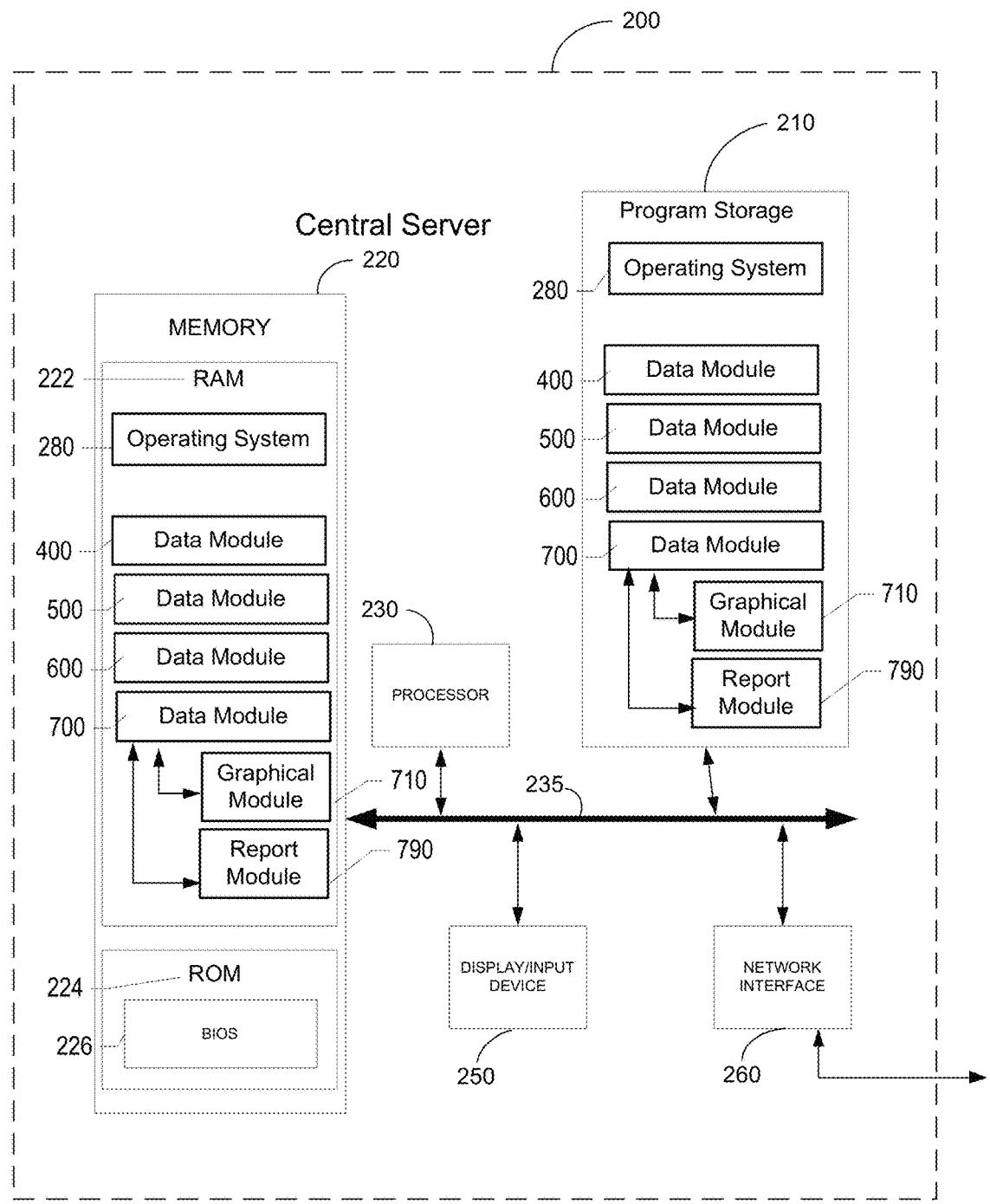
FIG. 2 is a schematic block diagram of a central server 200 according to various embodiments.
Figure 4A:
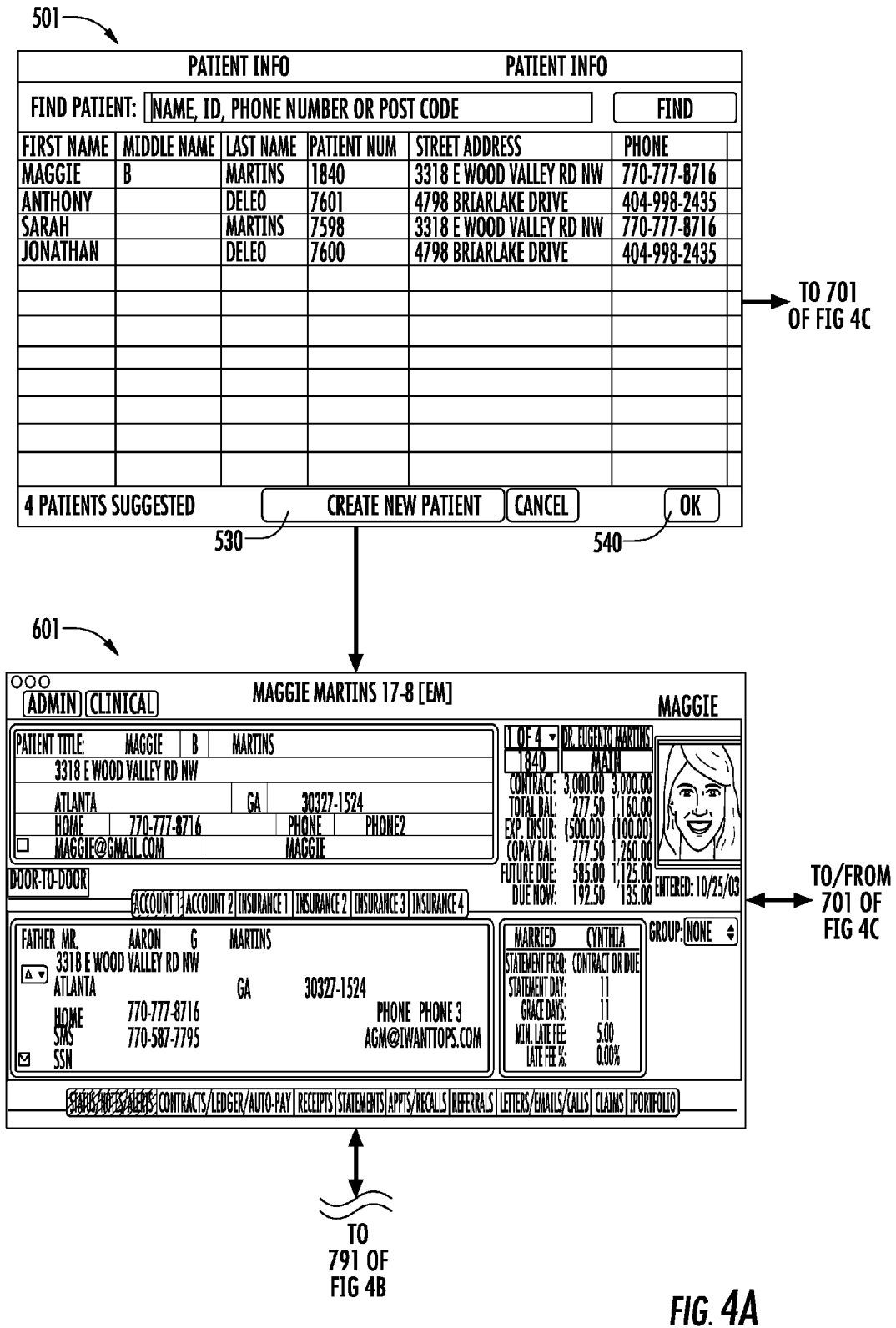
FIG. 4 is a flow chart of a user interface according to various embodiments.
Figure 4B:
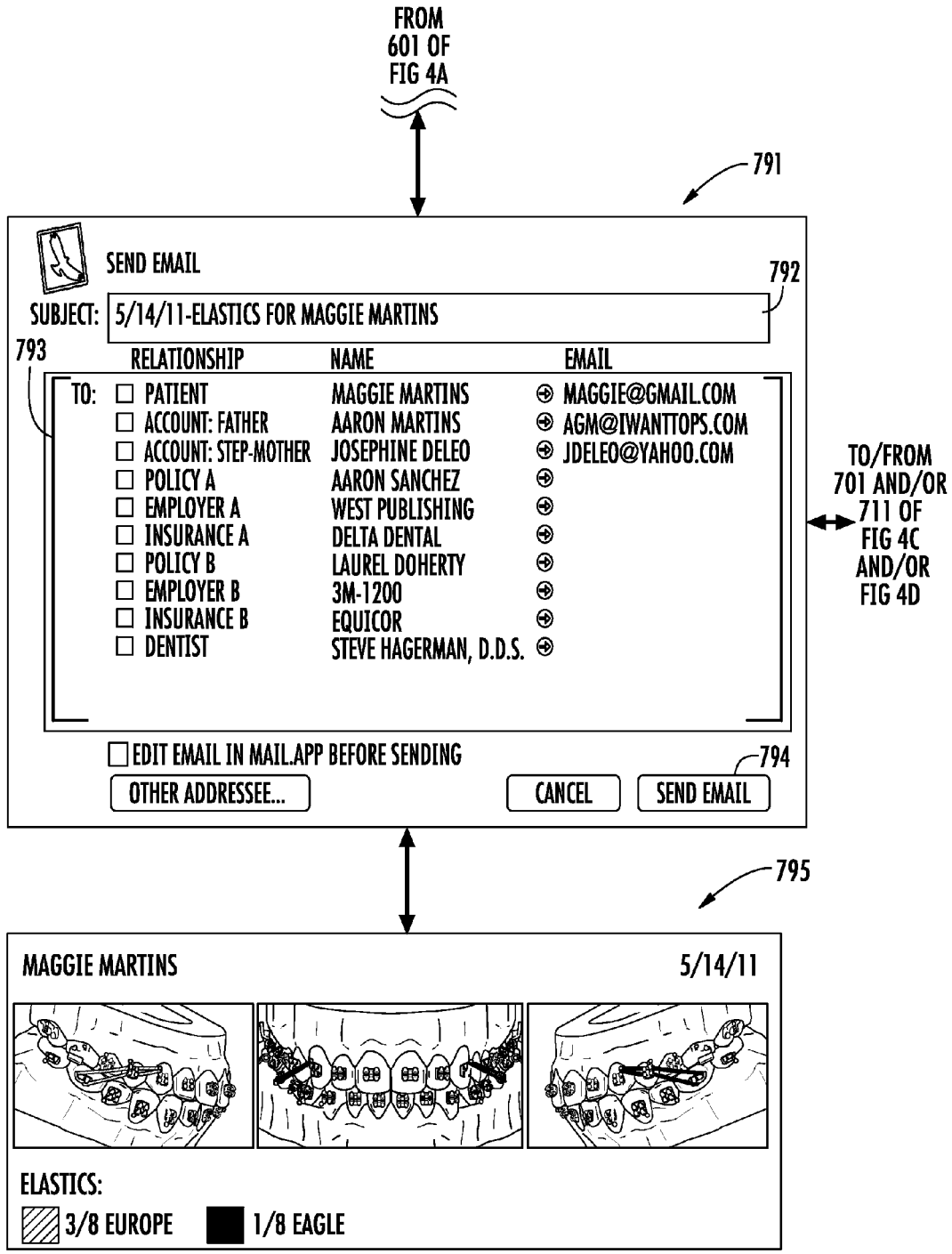
Figure 4C:
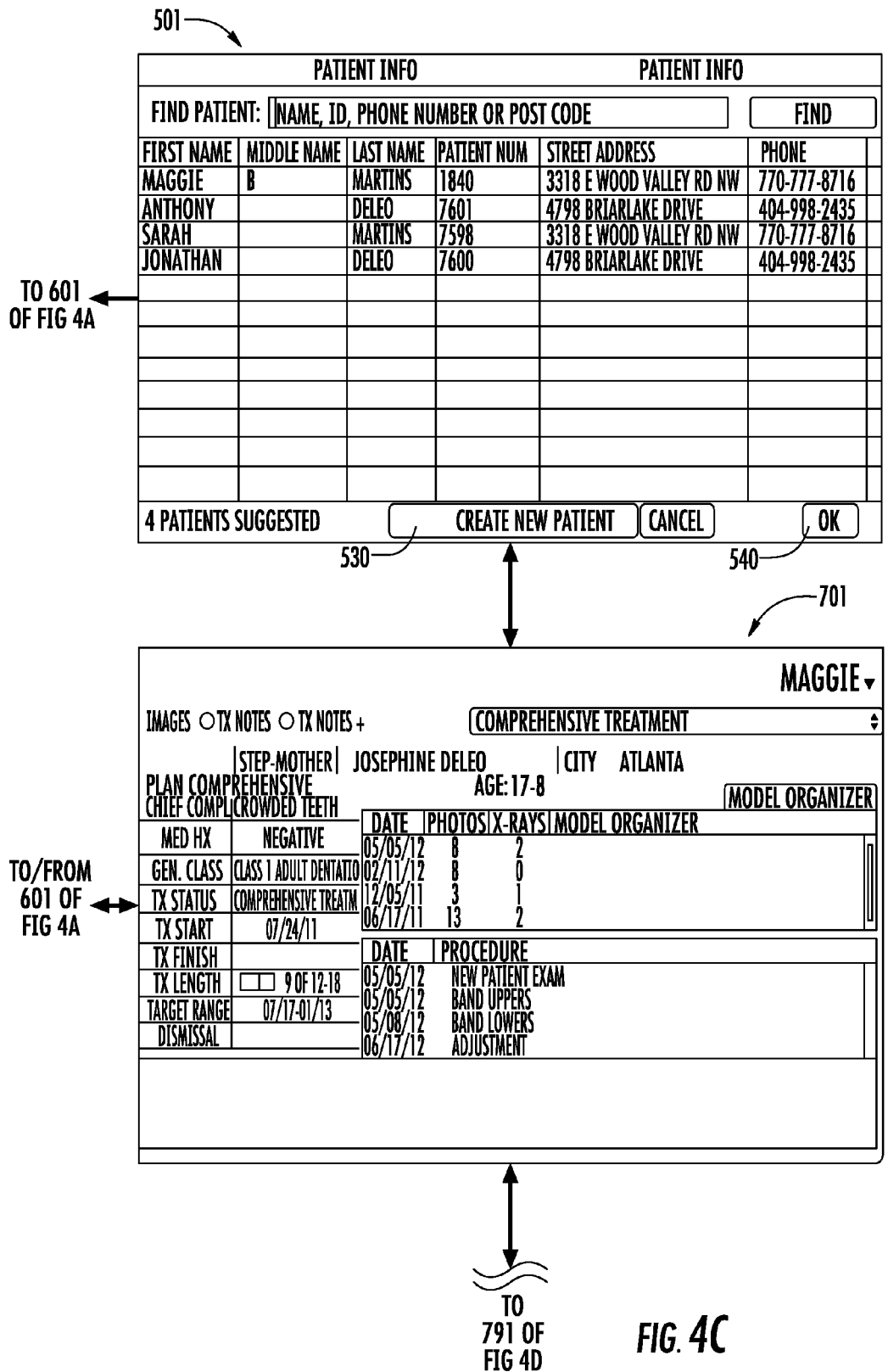
Figure 4D:
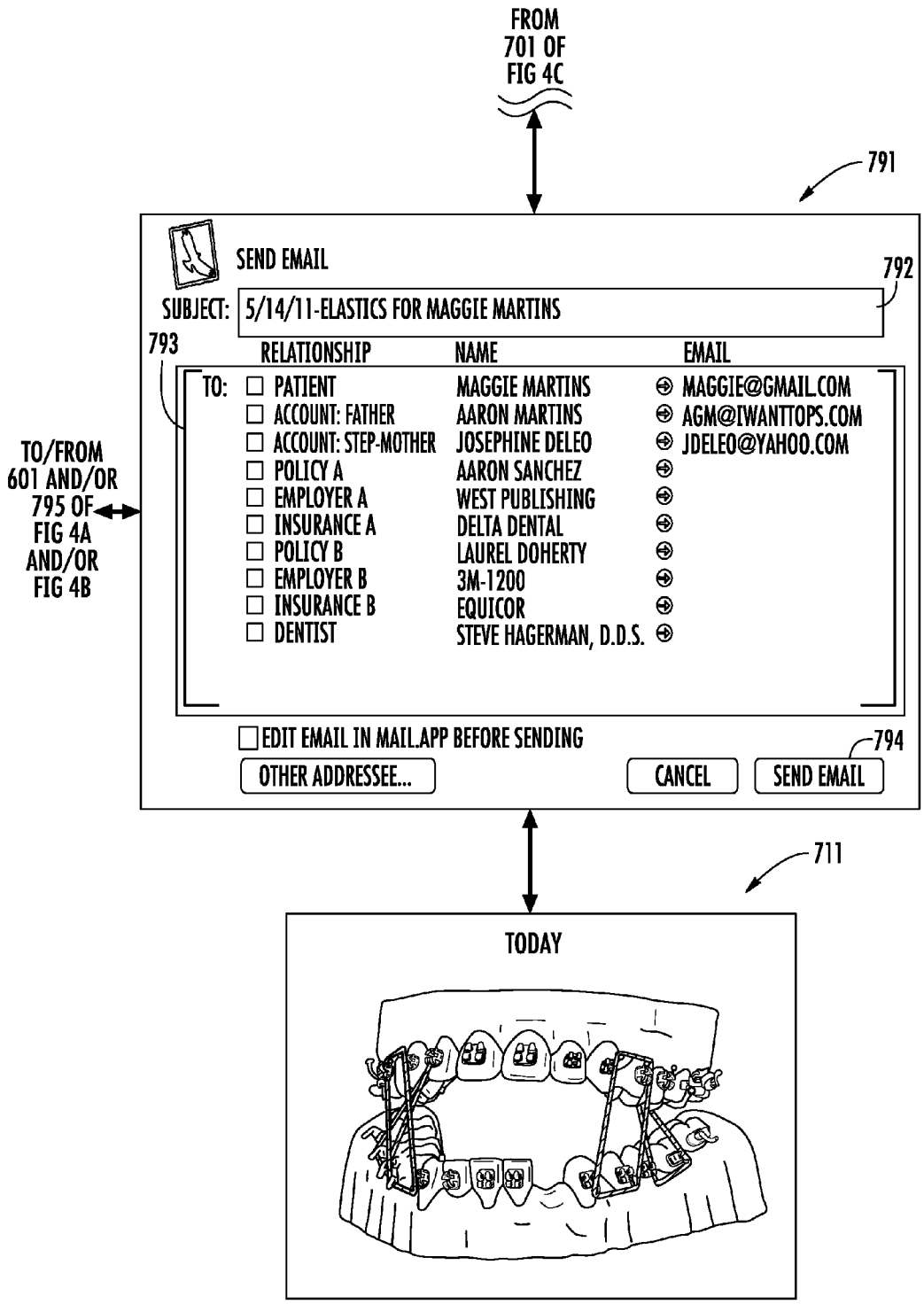

FIG. 2 is a schematic diagram of the central server 200 according to various embodiments. The server 200 includes at least one processor 230 that communicates with other elements within the server via a system interface or bus 235. Also included in the server 200 is at least one display/input device 250 for receiving and displaying data. This display/input device 250 may be, for example, a keyboard or pointing device that is used in combination with a monitor. The server 200 further includes a memory 220, which preferably includes both read only memory (ROM) 224 and random access memory (RAM) 222. The server's ROM 224 is used to store a basic input/output system 226 (BIOS), containing the basic routines that help to transfer information between elements within the server 200.

In addition, the central server 200 includes one or more storage devices 210, such as a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the art, each of these storage devices 210 are connected to the system bus 235 by an appropriate interface. The storage devices 210 and their associated computer-readable media provide nonvolatile storage for the central server. As will be appreciated by one of ordinary skill in the art, the computer-readable media described above could be replaced by any other type of computer-readable media known in the art. Such media include, for example, magnetic cassettes, flash memory cards, digital video disks, Bernoulli cartridges, and the like, as commonly known and understood in the art.

Also located within the central server 200 is a network interface 260 for interfacing and communicating with other elements of the one or more networks 130. It will be appreciated by one of ordinary skill in the art that one or more of the central server 200 components may be located geographically remotely from other server 200 components. Furthermore, one or more of the server 200 components may be combined, and/or additional components performing functions described herein may also be included in the server 200.

While the foregoing describes a single processor 230, as one of ordinary skill in the art will recognize, the central server 200 may comprise multiple processors operating in conjunction with one another to perform the functionality described herein. In addition to the memory 220, the processor 230 can also be connected to at least one interface or other devices capable of displaying, transmitting and/or receiving data, content or the like. In this regard, the interface(s) can include at least one communication interface or other devices for transmitting and/or receiving data, content or the like, as well as one or more user interface that can include a display and/or a user input interface. The user input interface, in turn, can comprise any of a number of devices allowing the entity to receive data from a user, such as a keypad, a touch display, a joystick or other input device.

While reference is made to a central "server" 200, as one of ordinary skill in the art will recognize, embodiments of the present invention are not limited to a client-to-server architecture. The system of various embodiments of the present invention is further not limited to a single server, or similar network entity or mainframe computer system. Other similar architectures including one or more network entities operating in conjunction with one another to provide the functionality described herein may likewise be used without departing from the spirit and scope of embodiments of the present invention. For example, a mesh network of two or more personal computers (PCs), similar electronic devices (e.g., laptops), and/or handheld portable devices, collaborating with one another to provide the functionality described herein in association with the server 200 may likewise be used without departing from the spirit and scope of embodiments of the present invention.

As illustrated in FIG. 2, a number of program modules may also be located within the central server 200. The program modules may be stored by the various storage devices 210 and within RAM 222. According to various embodiments, such program modules may include an operating system 280, a data module 400, a home module 500, an administrative module 600, and a clinical module 700. One or more of these modules 400, 500, 600, and 700, may comprise one or more additional modules (e.g., sub-modules), such as the non-limiting examples of a graphical module 710 and a report module 790, which may be configured to provide certain more detailed capabilities, as may be desirable in particular applications. As will be described in further detail below, according to certain embodiments, these modules 400, 500, 600, 700, 710 and 790 direct certain aspects of the operation of the server 200 with the assistance of at least the processor 230 and operating system 280.

With continued reference to FIG. 2, it should be understood that data module 400 may be configured to receive and store any of a variety of orthodontic practice management data, as will be described in further detail below. In certain embodiments, the data module 400 may be one or more internal databases configured to receive and store data, while in other embodiments, the data module 400 may be an internally stored spreadsheet or table-oriented program configured for efficient data handling processes. In still other embodiments, data received and/or stored by the system 5 may be stored in one or more shared databases, separate and distinct from any associated internal databases, so as to minimize and/or eliminate inadvertent release of sensitive patient and/or medical data. However configured, though, it should be understood that the data module 400 may interact with any of the remaining modules, as will be described in further detail below, such that orthodontic data is seamlessly and efficiently transferred there-between during operation and manipulation of the system 5 by a user.

In various embodiments, the one or more program modules 400, 500, 600, 700, 710 and 790 may be executed by the central server 200 and configured to, as a result, generate one or more graphical user interfaces accessible to users of the system 5. In one embodiment, the user interfaces may be accessible via one or more networks 130, which may include the Internet or other suitable communications network, as previously discussed. In other embodiments, one or more of the modules 400, 500, 600, 700, 710 and 790 may be stored locally on one or more distributed terminals 100 and/or handheld devices 120, and may be executed by one or more processors of the terminals 100 and/or devices 120. According to various embodiments, the modules 500, 600, 700, 710 and 790 may send data to, receive data from, and utilize data contained in, a database, which may be comprised of one or more separate, linked and/or networked databases, which may, in at least one embodiment be associated with the data module 400, as previously described herein.

Home Module 500

FIG. 3 is an exemplary view of a screen display 501 of the home module 500 according to various embodiments, as it may be displayed on, for example, the handheld device 120 and/or the distributed terminal 100, both as previously described herein. In certain embodiments, the screen display 501 of the home module 500 may appear automatically upon startup of the device 120 and/or terminal 100. In other embodiments, the user may need to access the home screen display 501 via one or more additional screens (e.g., software or program login screen or the like, all not shown) when preparing to activate and/or use the system 5.

In various embodiments, the screen display 501 of FIG. 3 may generally comprise a search field 510 and a result table 520. In certain embodiments, the search field 510 may be configured to permit a user (e.g., an orthodontist or employee/assistant thereof) to enter particular patient information so as to access and view any of a variety of data associated with the particularly associated patient. In at least the illustrated embodiment, common search parameters include name, ID number, phone number, and/or postal code, although in other embodiments, any of a variety of search parameters may be used to locate a patient record, as is commonly known and understood in the art.

Results of any submitted search parameters may be, according to various embodiments, returned in the result table 520, as also illustrated in FIG. 3. In certain embodiments, the result table 520 may return patient data in a patient record 521, which may include data such as the non-limiting examples of name, patient number, street address, and phone number. In other embodiments, it should be understood that any of a variety of data may be returned in the result table 520, provided such is of the type generally considered useful in identifying and distinguishing individuals relative to one another. In any of these embodiments, the patient record 521 of interest (e.g., if more than one returns) may be selected by the user in at least one of the table 520 itself and a selection button 540, as also commonly known and understood in the art. As will be described in further detail below, selection of button 540 and/or a particular patient in table 520 will, according to various embodiments, activate a screen display 601 associated with the admin module 600. Of course, in other embodiments, any of a variety of more detailed screen displays may be activated upon patient selection, as is commonly known and understood in the art.

Remaining with FIG. 3, it should be further understood that the screen display 501 may, according to various embodiments, comprise a button 530 configured to permit the creation of a new patient record. Such may selected by a user, either upon initial activation of the home module 500 or upon a failure to locate a particular patient via the search field 510 and parameters entered therein. Of course, still other embodiments, may, without departing the scope of the present invention, include any of a variety of startup and patient location, search, and entry screen displays, as such are generally commonly known and understood in the art.

Turning now to FIG. 4, a flow chart according to various embodiments is provided that depicts the logic flow employed for communication between the various program modules located within the central server 200. It should be understood that this logic flow may in certain embodiments be conducted manually, automatically, or any combination thereof, as may be desirable for particular applications.

As may be best understood from FIG. 4, a user may, when seeking to access information regarding a particular patient, according to various embodiments, access the admin module 600 via the home screen display 501. In certain embodiments, when such occurs, a screen display 601 of the admin module 600 appears. In these and still other envisioned embodiments, the screen display 601 may likewise contain a plurality of selectable (e.g., touch activated) icons, each representing any of a variety of patient care and/or practice management tasks and data associated therewith, as will be described in further detail below.

From the screen display 601 of the status module 600, the user may, according to various embodiments, select one of a plurality of icons, as will be described in further detail below, to obtain further information regarding any of a variety of administrative-related data (e.g., alerts, financial and billing data, statements, appointments, referrals, correspondence, insurance claims, and the like). When such is done, individualized screens 610-660 will appear in portion 603 of display 601 (see also FIG. 5), providing additional detail for the user, all as will be described in further detail below.

Remaining with FIG. 4, it may be understood that the user, if desiring detailed information regarding diagnosis and/or treatment of a patient (or alternatively, to record data concerning ongoing actions), may according to various embodiments select an icon on the admin screen display 601 that will direct the user to the screen display 701 of the clinical module 700 (see also FIG. 8). Depending on a particular scenario, it should be understood that the screen display 701 of the clinical module 700 may be accessed directly from the screen display 501 of the home module 500. In accordance with certain embodiments, the screen display 701 may incorporate or otherwise interface with a screen display 711 of the graphical (sub)module 710 of the clinical module 700. In these and still other embodiments, the displays 601, 701 may be, in essence, toggled relative to one another, as may be desirable for particular applications.

According to various embodiments, the screen display 711 of the graphical (sub)module 710 may be configured such that a user may select an icon, as will be described in further detail below, which may be configured to cause a screen display 791 of a report module 790 to appear. From the screen display 791, the user may generate one or more reports (e.g., 795, 795A, etc.), which may be transmitted via any of a variety of mediums (e.g., email, USPS, etc.), as may be desirable for particular applications. It should be understood that the screen display 791 of the report module 790, while described later herein primarily as being accessed via the screen display 711 of the graphical (sub)module 710, such may, in other embodiments, be accessed additionally and/or alternatively via one or more of the screen displays 701 and 601.

It may be further understood from FIG. 4 that, when accessing the screen display 711 of the graphical (sub)module 710 of the clinical module 700, the screen display may be configured to permit the user to manipulate the graphical depiction thereon of a patient's teeth and associated orthodontic hardware (e.g., brackets, elastics, and the like). As will be described in further detail below, such manipulation may include the non-limiting examples of applying or removing brackets, applying or removing elastics, rotating the view of the teeth in a substantially horizontal plane, opening the teeth in a substantially vertical plane, and/or selectively removing or inserting teeth.

Admin Module 600

According to various embodiments, the admin module 600 is generally configured to provide an efficiently integrated tool for the electronic management of the administrative aspects (e.g., scheduling, financial payment, correspondence, and patient info) of an orthodontic practice. While it should be understood that various electronic administrative practice management capabilities and associated systems are commonly known and understood in the art, the description thereof herein is provided as an exemplary configuration for purposes of providing a legally sufficient disclosure.

Turning now to FIG. 5, an exemplary screen display 601 of the admin module 600 according to various embodiments may be seen, as such may be displayed on, for example, the handheld device 120 and/or the distributed terminal 100. In certain embodiments, as has been described previously herein, the admin module 600 may be activated by a user via the home module 500. Of course, in other embodiments, the admin module 600 may be configured to itself be a "home screen," containing therein search fields for locating, identifying, and retrieving data regarding one or more patients. Illustrated icon 605 may, according to various embodiments, may be configured to facilitate toggling between the screen display 601 of the admin module 600 and a screen display 701 of a clinical module 700, as will be described in further detail below.

With continued reference to FIG. 5, it should be understood that various embodiments of the screen display 601 generally comprise at least one of a patient summary field portion 602, a patient account field portion 604, and a detailed data field portion 603. Each of these portions may be populated with any of a variety of data from the data module 400, e.g., the non-limiting examples of patient name, address, phone, postal code, email, bank account information, insurance policy information, appointment data, billing and accounting information, referral information, correspondence records, and a list of claims filed by the patient. Of course, any combination of data may be displayed or retrieved via any one of the portions 602-604, as may be desirable for particular applications, and the particular embodiment illustrated in FIG. 5 is intended for exemplary purposes only, as such administrative data management modules and associated programs and systems are generally commonly known and understood in the art.

FIG. 5 likewise illustrates that, in accordance with various embodiments, the detailed data field portion 603 may be toggled between displays of various information by a user's selection of one or more icons 610-660, which will be addressed in turn below. It should be noted, however, that such icons for accessing and displaying any of a variety of administrative-related patient data is commonly known and understood in the art, but described herein for purposes of a complete disclosure.

Firstly, FIG. 5 displays a status icon 610 configured according to various embodiments to display patient data related to billing and appointment reminders, critical events in the patient's life that might impact treatment, and the like. A set of financial icons 620, 622, and 624, configured in certain embodiments to display contracts, ledger, receipts, billing statement data, and the like, providing a concise and accurate compilation of financial related patient data for effective and efficient use and reference, may also be provided. Additional icons 630, 640, 645, 650, and 660, may be respectively configured according to various embodiments to display appointment and calendar data, referrals (e.g., in and/or out of the user's practice), correspondence conducted with individual patients or otherwise (e.g., by email and the like, as will be described in further detail elsewhere herein), claims submitted to the patient's insurance provider (e.g., by the patient and/or the user), and a portfolio compiling useful and pertinent patient documents related not only to administrative, but in certain embodiments also clinical-related data.

Clinical Module 700

According to various embodiments, the clinical module 700 is generally configured to provide an efficiently integrated tool for the electronic management of the medical diagnosis and treatment aspects of an orthodontic practice. While it should be understood that certain electronic treatment plan management capabilities and associated systems are commonly known and understood in the art, various features described herein provide additional and/or improved capabilities by comparison thereto.

Turning now to FIGS. 6-7, with at least initial emphasis upon FIG. 6, an exemplary screen display 701 of the clinical module 700 according to various embodiments may be seen, as such may be displayed on, for example, the handheld device 120 and/or the distributed terminal 100. In certain embodiments, as has been described previously herein, the clinical module 700 may be activated by a user via the home module 500, while in other embodiments the clinical module may be activated and accessed via the admin module 600. In still other embodiments, the clinical module 700 may be configured to itself be a "home screen," containing therein search fields for locating, identifying, and retrieving data regarding one or more patients, as may be desirable for particular applications. In any of these and still other embodiments, it should be understood that the illustrated icon 705 may be configured to enable toggling between the respective displays of the admin and clinical modules 600, 700, as may be desirable for a particular application. Of course, any of a variety of icons or the like may be provided to permit such toggling, and the illustrated icon should be considered exemplary in this regard.

Referring now more broadly to FIGS. 6-7, it should be understood that various embodiments of the screen display 701 generally comprise a plurality of selectable icons 706, each configured to navigate a user to associated data field portions 702, 703, 704, and 707. As a non-limiting example, FIG. 6 illustrates data field portion 702 configured to display a variety of general patient treatment data, such as name, age, historical treatment dates, projected treatment completion dates, and the like. The data field portion 703, also in FIG. 6, illustrates additional textual detail regarding the ongoing diagnosis and treatment plan for a particularly selected patient, down to the level of, for example, teeth extraction notes, types of arch-wires and brackets applied, and additional comments. The treatment notes of data field portion 707 of FIG. 7 may according to various embodiments, provide a variety of in-depth historical treatment data, as compared to the futuristically focused data of field portion 703. However, it should be understood, that together, these field portions 702, 703, and 707 provide textual-based detailed treatment and diagnosis data (e.g., as retrieved from the data module 400) for use by an orthodontist during the course of treating a patient.

With particular focus on FIG. 7, a data field portion 704 is further illustrated, which may be configured to display a variety of patient treatment images for use as visual aids with reference to the previously described textual data of field portions 702, 703, and 707. According to various embodiments, the images that may be displayed in data field portion 704 may include the non-limiting examples of photographs of a patient's teeth from a variety of perspectives (see e.g., those illustrated in FIG. 7), images of tooth models made of the patient's teeth, x-ray images taken of the patient's head and/or teeth, and/or graphical models of the patient's head. It should be understood that still other embodiments, may incorporate any of a variety of alternatives images, provided such may prove useful in the efficient and effective treatment of orthodontia on the patient's teeth, as will be described in further detail below. It should be further understood that in any of these embodiments, one or more of the images displayed in data field portion 704 may likewise be referenced to create a three-dimensional model of the patient's teeth, as will be described in detail below.

Graphical (sub)Module 710

With reference now to FIG. 8, according to various embodiments, at least one of the plurality of selectable icons 706 of the screen display 701 of the clinical module 701 may be configured navigate a user to an associated screen display 711 of a graphical (sub)module 710 of the clinical module. In certain embodiments, the screen display 711 of the graphical module 710 may incorporate a "split-screen" display, enabling a user to view and access not only the screen display 711 but also at least certain features of the screen display 701 of the broader clinical module 701. For example, in FIG. 8, it may be seen that the screen display 711 may be configured in these and other embodiments to display not only a three-dimensional (3-D) model 715 of a patient's teeth, but also one or more of the data field portions (e.g. 702, 703, 704, and 707) associated with the screen display 701.

While in at least the illustrated "split screen" embodiment of FIG. 8, the 3-D model 715 appears above at least the data field portion 707, other embodiments may be displayed alternatively (whether vertically tiled, horizontally tiled, cascaded, or otherwise), as may be desirable for particular applications. With reference to FIG. 15, however, it should be further noted that the "split-screen" display feature of FIG. 8 may be toggled "on" or "off", as may be beneficial where, for example, a larger and/or more detailed view of the 3-D model may be desirable.

Returning now to FIG. 8 and with reference to the 3-D model 715 in particular, according to various embodiments, the 3-D model may be generated by any of a variety of commonly known and used 3-D rendering or computer graphics processes, including the non-limiting examples of contour modeling, spline modeling, digital sculpting, procedural modeling, image-based modeling, and 3D scanning. While these and still other modeling methods use slightly differing procedures, as are generally commonly known and used in the art, each incorporate meshes and/or grids that may be used to define a plurality of discrete points (typically across an x, y, z cloud), which are in turn associated with particular design elements. For example, with reference to at least the illustrated embodiment of FIG. 8, each of the illustrated teeth 712 may be defined by a plurality of discrete points located thereupon (e.g., whether on the outside surface, a top surface, or an inside surface, as will be referenced later herein).

Continuing with the example, in certain embodiments, particular discrete points are associated with specific design elements of a particular tooth 712, such that the tooth, as a whole and still further within the model 715 in its entirety may be manipulated to simulate movement thereof, also as will be described in further detail below. It should be understood, of course, that in any of these and still other embodiments, the plurality of discrete points that define the 3-D model 715 may be obtained via any of the previously mentioned rendering or modeling techniques, which may, in at least one embodiment, comprise rendering the model from one or more images such as those shown in FIG. 7 and previously described herein.

Returning now to FIG. 8, according to various embodiments, the screen display 711 of the graphical module 710 may display at least a bracket tool 720, an elastic tool 730, and a report tool 780. While in certain embodiments (as illustrated), each of these tools may be embedded within the 3-D model 715, it should be understood that in other embodiments, the tools may be separately or otherwise displayed, as may be desirable for particular applications. However, in any of these or still other embodiments, at least the bracket tool 720 and the elastic tool 730 are generally configured to facilitate the placement of any of a variety of elements (e.g., brackets, elastics, arch-wires, retainers, expansion appliances, trans-palatal bars, or the like) commonly known and used in the course of orthodontic treatment plans.

According to various embodiments, when selected (e.g., touched or clicked upon by a user), each of the tools 720, 730, and 790, and the like may be configured to display a new window containing user-selectable options for the selection and/or creation of elements for placement on the 3-D model 715, as will be described in further detail below. In certain embodiments, the new window (not shown) may be a "pop-up" window that contains a listing of element options for a user to choose between. For example, if the bracket tool 720 is selected, an associated "pop-up" window 910 (see FIG. 19A) may appear atop or substantially adjacent the 3-D model 715, listing various types or colors of brackets 725 that may be, in turn, selected for actual placement upon the model, all as will be described in further detail below. Likewise, if the elastics tool 730 is selected, an associated "pop-up" window 960 (see FIG. 19B) may appear atop or substantially adjacent the 3-D model 715, listing various types or colors of elastics 732 that may be, in turn, selected for actual placement upon the model. It should be understood, however, that in any of these and still other embodiments, the selection of each of the tools may be otherwise configured without departing the scope of the present invention, provided such continues to facilitate use of the 3-D model in an efficient and effective manner.

Bracket Tool 720

With continued reference to FIG. 8, the bracket tool 720 may be configured according to various embodiments to facilitate the placement of one or more brackets 725 on one or more teeth 712 depicted in the 3-D model 715. In certain embodiments, the one or more brackets 725 may be individually selected from a group of commonly known and used brackets 912 (e.g., based upon function, configuration, or the like as illustrated in FIG. 19A), while in other embodiments, the one or more brackets 725 may be custom configured and/or selected. In these and still other embodiments, the various commonly known and used bracket configurations, together with any custom built bracket configurations (see also FIG. 19A) may be saved for future use via the bracket tool 720. Still further, in any of these and other embodiments, the various brackets 725 may be named, color coated, and the like, so as to clearly and efficiently distinguish there-between when referencing the 3-D model 715.

According to various embodiments, as illustrated in at least FIGS. 8-15, a user accessing the bracket tool 720 may place one or more brackets 725 upon one or more teeth 712 depicted in the 3-D model 715 by selecting (e.g., touching upon, clicking upon, or the like) the particular teeth upon which a bracket is desired. In certain embodiments, selection of the particular teeth is associated with selection of certain of the plurality of discrete points forming the interactive 3-D model 715, as previously described herein, such that the brackets 725 may be precisely and accurately placed in various positions upon the teeth. In at least the illustrated embodiment, it may be seen that the brackets 725 may be substantially centrally placed on the outside surface of the teeth (e.g., that surface of the teeth facing outward and visible when a patient's mouth is open), as defined by at least one discrete point thereupon. However, in other embodiments, it should be understood that the brackets 725 may be placed via one or more discrete points located on the inside surface of the teeth, which surface may be seen in, for example FIGS. 17 (but with no brackets thereupon). In still other embodiments, it should be understood that multiple discrete points on either the outside or inside surface of the teeth may be configured for customizable bracket placement (e.g., such that the bracket may be placed higher/lower or left/rightward upon the tooth), as may be desirable for particular applications.

Turning now to FIG. 19A with continued reference also to FIG. 8, the bracket tool 720 may be configured with multiple methods of placing the one or more brackets 725 upon the one or more teeth 712 of the 3-D model 715. As has been described herein, the particular bracket 725 (e.g., defined by one or more of color-coding, type, name, or the like) may be first selected from window 910 (e.g., by touching upon, clicking upon, or the like), after which the bracket may be placed upon a single tooth or, alternatively upon multiple teeth. In certain embodiments, the bracket tool 720 may be configured with a "repeat feature," which may be configured to retain the particularly selected bracket for "repeat" placement upon multiple teeth, thus eliminating the need to reselect the bracket for each individual placement desired. In at least one of these embodiments, the repeat feature may be configured to retain the particularly selected bracket for approximately 1.5 seconds, while in other embodiments, any relatively brief period of time (e.g., up to perhaps 5 seconds or more) may be utilized. In still other embodiments, the duration of the repeat feature may be customizable by the user to any of a variety of durations, as may be beneficial for particular applications. However, in any of these and still other embodiments, it should be understood that upon expiration of the predetermined duration of the "repeat feature," the user would need to reselect any additional particular brackets for placement upon remaining teeth.

According to various embodiments, as has been generally described above, the bracket tool 720 may be configured for individual and separate placement of brackets 725 upon at least some portion of the teeth 712 of the 3-D model 715. As also mentioned, certain embodiments of the bracket tool 720 may incorporate a "repeat feature" to facilitate more efficient bracket placement, where a single selected bracket 725 may be placed upon multiple teeth without reselection thereof for each tooth, also as previously described herein. Still other embodiments of the bracket tool 720, however, may further comprise an option 914 in window 910 (see FIG. 26A) to place brackets upon all teeth in a single action. Additionally, in any of these embodiments of the bracket tool 720 the window 910 may further facilitate bracket removal 916, which may similarly be performed one tooth at a time, with or without a corresponding "repeat removal" feature, or all at once, as has been described previously herein in the context of bracket placement.

Lastly, and with reference primarily to FIG. 14, according to various embodiments, the bracket tool 720 may be further configured to selectively remove one or more teeth (e.g., leaving a cavity 770) from the interactive 3-D model 715. In certain embodiments, the bracket tool 720 may open a "pop-up" window 910 (see also FIG. 26A) comprising a selectable menu containing a "remove tooth" option 918. Once selected, a user of the bracket tool 720 may select (e.g., touch upon, click upon, or the like) particular teeth for removal. Notably, in comparison to certain prior art systems, which only enable placement of a "red X" (or some comparable "removal" denotation) upon the tooth, actual removal provides an improvement because, for example, when a particular patient has had one or more teeth removed for purposes of creating sufficient space for movement of the remaining teeth as part of an orthodontic treatment plan, such movement may be realistically simulated by the interactive 3-D model 715 if the teeth are actually removed.

Of course, it should be understood that in addition to facilitating the removal of teeth from the interactive 3-D model 715, as may be desirable for particular applications, the bracket tool 720 may similarly be configured to place teeth, whether upon initial creation of a patient model or otherwise. In this regard, certain embodiments may be configured, much as previously described herein, with a "pop-up" window 910 (see again FIG. 19A) comprising a selectable menu containing a selectable "place tooth" option 920. Once selected, the user of the bracket tool 720 may select (e.g., touch upon, click upon, the like) particular locations within the model for placement of teeth. In other embodiments, an option may exist for the user to select an option to "place all teeth," which may provide a beneficial time-saving option when, for example, creating an initial patient model. In any of these and still other embodiments, however, it should be understood that while the teeth placement and removal feature has been described with regard to the bracket tool 720, a separate and distinct tool, either within the 3-D model 715 or displayed adjacently thereto on screen display 711 (see FIG. 14 again) may be provided, as may be desirable for particular applications.

Elastic Tool 730

Turning now to FIG. 9, the elastic tool 730 may be configured according to various embodiments to facilitate the placement of one or more elastics 732 (e.g., rubber bands) on one or more teeth 712 (see FIG. 15) depicted in the 3-D model 715. In certain embodiments, the one or more elastics 732 may be individually selected from a group of commonly known and used elastics 962 (e.g., based upon function (high/low torque, etc.), configuration (e.g., walrus, elephant, etc.), or the like as illustrated in FIG. 19B), while in other embodiments, the one or more elastics 732 may be custom configured 964 (e.g., left class II, right class II, etc.) and/or selected. With reference to FIG. 11, it should be understood that certain customized elastics configurations 737 may be saved and/or predetermined by a user, such that their placement upon two or more teeth may be performed with a single motion, as will be described in further detail below. In these and still other embodiments, it should be understood that the various commonly known and used elastic configurations, together with any custom built elastic configurations may be saved for future user selection via the elastic tool 730, so as to at least in part simplify the process for applying, adjusting, and/or removing the same. Still further, in any of these and other embodiments, the various elastics 732 may be named, color coded, and the like, so as to clearly and efficiently distinguish there-between when referencing the 3-D model 715, as was also previously described herein for the associated brackets.

According to various embodiments, as illustrated in at least FIGS. 9-15, a user accessing the elastics tool 730 may place one or more elastics 732 upon one or more teeth 712 depicted in the 3-D model 715 by selecting (e.g., touching upon, clicking upon, or the like) the particular teeth upon and between which an elastic is desired. In certain embodiments, selection of the particular teeth is associated with selection of certain of the plurality of discrete points forming the interactive 3-D model 715, as previously described herein, such that the elastics 732 brackets 725 may not only be precisely and accurately placed relative to the brackets 715 but also the teeth themselves. In at least the illustrated embodiment, it may be seen that the elastics 732 may be substantially centrally "fixed" to the surface of a first bracket by clicking thereupon, after which the elastic may be "strung" or extended between that bracket and an adjacently positioned (or merely nearby) second bracket. In other embodiments, the elastics 732 may be "fixed" relative to an appendage of a particular bracket, as is commonly known and understood in the art. It should be understood that in any of these and still other embodiments, the elastics 732 may be fixed to two or more brackets however those brackets may be placed upon respective surfaces of various teeth 725, as previously described herein.

Turning now to FIG. 19B with continued reference also to FIG. 6, the elastics tool 730 may be configured with multiple methods of placing and stretching the one or more elastics 732 on and between the one or more teeth 712 of the 3-D model 715. As has been described herein, a particular elastic 732 (e.g., defined by one or more of color-coding, type, name, function or the like) may be first selected from window 960 (e.g., by touching upon, clicking upon, or the like), after which the elastic may be placed upon a single tooth 734 (see FIG. 10). Once initially fixed to the single tooth 734, the elastic may be manipulated by the user to stretch onto another tooth 736 (see also FIG. 10). Such manipulation may occur by touching or clicking upon the secondary tooth, at which point the elastic will be displayed in the 3-D model 715 as passing between those two respective teeth. It should be understood that in these and still other embodiments, the 3-D model 715 may be configured such that the plurality of discrete points to which the brackets 725 and in turn the elastics 732 are fixed should substantially prevent the appearance of the passage of the elastics 732 through the interior of any respective teeth. Such will be described in further detail below in the context of further model manipulation capabilities such as the opening and closing of the teeth without the elastics passing through the interior of any teeth.

With reference momentarily to FIG. 11, it should be understood that according to various embodiments one or more customized elastics configurations 737 may be pre-saved (e.g., via the process described with respect to FIG. 19B). In such instances, the elastics tool 730 may be further configured so as to facilitate more efficient placement of such elastic configurations 737 by not only saving the configuration, but also the design thereof, including the particular teeth upon which placement is typically desired. As a result, instead of having to sequentially select individual teeth between which the elastic configuration 737 is to be strung, the user may instead, via the elastics tool 730 select the desired elastic configuration 737 and subsequently click upon any portion of the 3-D model 715, in response to which the elastic configuration will be automatically strung between the pre-saved teeth. As a non-limiting example, a right side box elastic 737 may be prepopulated and saved for later use, as such is generally illustrated in at least FIG. 11. Of course, in these and still other embodiments, upon initial placement of the "strung" configuration, the elastics tool 730 may be configured to permit further user customization and/or manipulation of the particular placement of the elastic configuration 737, as may be desirable for certain applications.

Returning to FIG. 19B, in various embodiments, the elastics tool 730 may be configured with a "repeat feature," which would retain the particularly selected bracket for "repeat" placement upon multiple (e.g., more than two) teeth. In at least one of these embodiments, the repeat feature may be configured to retain the particularly selected elastic for approximately 1.5 seconds, while in other embodiments, any relatively brief period of time (e.g., up to perhaps 5 seconds) may be utilized. In still other embodiments, the duration of the repeat feature may be customizable by the user to any of a variety of durations, as may be beneficial for particular applications. However, in any of these and still other embodiments, it should be understood that upon expiration of the predetermined duration of the "repeat feature," the user would need to reselect any additional particular elastics for placement upon any remaining teeth lacking elastics. It should also be understood that in those embodiments containing pre-saved "strung configurations" as previously described herein, the repeat function may be similarly configured to place the elastic configuration 737 across multiple teeth, without the need for individual selection thereof. Of course, any of a variety of configurations for elastics placement may be envisioned, without departing from the scope and nature of the various embodiments described herein.

According to various embodiments, as has been generally described above, the elastics tool 730 may be configured for individual and separate placement and stretching of elastics 732 upon and between at least some portions of the teeth 712 of the 3-D model 715. Certain embodiments of the elastics tool 730 may incorporate the "repeat feature" described above to facilitate more efficient bracket placement, where a single selected elastic 732 may be placed upon multiple teeth without reselection thereof for each tooth, also as previously described herein. Still other embodiments of the elastics tool 730, however, may further comprise an option 968 in window 960 (see FIG. 19B) to place elastics upon a predetermined set of teeth in a single action. Additionally, in any of these embodiments of the elastics tool 730, the window 960 may further facilitate elastics removal 966, which may similarly be performed one tooth at a time, optionally with a repeat feature, or all at once, as has been described previously herein in the context of bracket placement.

Returning for a moment to FIG. 8, it should be understood that while various embodiments of the interactive 3-D model 715 of a patient's tooth chart have been described previously herein as comprising a bracket tool 720, an elastic tool 730, and a report tool 780, still other embodiments of the model may comprise additional tools, as may be desirable for particular applications. As a non-limiting example, in certain embodiments, the 3-D model 715 may further comprise an arch-wire tool, which may be configured to facilitate placement of any of a variety of arch-wires, as commonly known and used in the art, through the plurality of brackets 725 placed upon the modeled teeth 712. Of course, in other embodiments, the arch-wire tool (or any other tools) may be incorporated within the bracket tool 720, as may be desirable for particular applications. However, in any of these and still other embodiments, it should be understood that the arch-wires may be color-coated, named, customized, and/or positioned upon the 3-D model 715 in any of the variety of fashions as previously described herein in the context of brackets 725 and/or elastics 732.

Lastly, it should be understood that, in addition to arch-wires, various embodiments of the interactive 3-D model 715 of a patient's tooth chart may be configured with specialized tools to facilitate proper placement of any of a variety of elements used during the course of traditional orthodontic treatment plans. Such elements may include the non-limiting examples of retainers, expansion appliances, trans-palatal bars, and the like, which case any and all of the same may be color-coded, named, customized, and/or positioned upon the 3-D model 715 in any of the variety of fashions as previously described herein in the context of brackets 725 and/or elastics 732.

Manipulation of Interactive 3-D Model 715

According to various embodiments, with reference generally to FIGS. 8, 9, and 12, the interactive 3-D model 715 may be configured to permit a user to manipulate the tooth model depicted therein into any of a variety of orientations via, for example, movement imposed upon the model (e.g., via a cursor and mouse action, via touch movement by a user, or the like). In certain embodiments, the imposed movement may cause the 3-D model 715 to rotate the tooth model to the left or the right substantially in a horizontal plane (see e.g., the combination of FIGS. 12-13). In these and other embodiments, imposed movement may cause the 3-D model 715 to rotate through any of a variety of planes and/or degrees of freedom.

Turning now in particular to FIG. 8, the 3-D model 715 according to various embodiments may display the tooth model in a closed-tooth configuration 740, wherein the top and bottom teeth are substantially touching relative to one another. When in this closed-tooth configuration 740, however, certain embodiments of the 3-D model 715 may be configured so as to permit a user to open either the top (see FIG. 9) or the bottom (see FIG. 12) teeth, as may be desirable for particular applications. When in such a "top open" 750 configuration or a "bottom open" 760 configuration, it should be understood it may be possible to impose rotation of the tooth model left or right or through any of a variety of degrees of freedom, as previously described herein in the context of the "closed-tooth" configuration and as will be described elsewhere with reference to at least arrows 811 and 812.

According to various embodiments, the "top open" configuration 750 of FIGS. 9-10 may be achieved by scrolling (e.g., via a mouse/cursor, touch, or the like) upward on the model 715 in the direction indicated by arrow 810. In certain embodiments, as the scrolling in the direction indicated by arrow 810 occurs, the top teeth progressively hinge open, while the bottom teeth move downward within the model. It should be understood that in these and other embodiments, such a "dual motion" when scrolling in the direction indicated by arrow 810 enables opening of the top teeth without the need to resize the window in which the model 715 appears. In other words, the "dual motion" feature allows the view of model 715 to be smaller vertically yet still allow good visibility to the inside of the upper teeth when open. Of course, in still other embodiments (see FIG. 15), in which the model window may be enlarged, such dual motion may be optional, as may be desirable for particular applications.

According to various embodiments, as may be seen in FIGS. 9-10, anywhere in the "top open" configuration 750, the model 715 may be further manipulated by movement in the direction of arrows 811 and 812, facilitating viewing perspectives of the tooth model from left, right, and anywhere there-between, as may be desirable for particular applications. Such is also possible when in the closed configuration 740, as previously described herein. In certain embodiments, it should be noted that when in the "top open" configuration 750, the elastics 732 passing between teeth 734, 736 may be configured to sequentially "snap" to successive discreet points upon the teeth (as previously described herein), so as to prevent the elastics 732 from ever passing through the interior of the teeth, even during progressive opening of the top teeth relative to the lower teeth and/or manipulation thereof via one or more planes of movement. In other embodiments, the manner in which the elastics 732 snap to particular discreet points upon the teeth may be further configured such an the elastics 732, upon manipulation, wrap around the edge of the upper tooth 736 (see FIGS. 10 and 11 specifically) rather than passing through the body of the upper tooth.

In various embodiments, the successive discreet points are positioned along the incisal edges of the upper incisors and activated when elastic 732 connects between two anterior teeth, one upper and one lower (see FIG. 10). In other embodiments, the successive discreet points are positioned along the posterior teeth, which allows posterior cross-bite elastics to wrap around the cusps of the upper and lower posterior teeth when connected from upper to lower with the connection passing from an inside to an outside tooth surface. Of course, still other embodiments may incorporate any of a variety of configurations, as associated with any of a variety of teeth located within the model 715, provided such similarly facilitate substantially preventing passage of elastics 732 through the interior of any teeth of the model 715.

With continued reference to FIGS. 9-11 and also FIG. 12, it should be understood that in various embodiments, the "dual motion" feature described above, when hinging open the top teeth and moving downward the lower teeth, may be further configured so as to simultaneously "flare out" the upper and/or lower arches so that the "back teeth" portion of the model 715 are more visible from a front view than they would be if the arches were anatomically precise. This is particular evident in at least FIG. 12. As may be seen from also FIG. 9, such movement may also facilitate better visibility of the chewing surfaces of the teeth in the "top open" configuration 750, while also improving visibility of the inside of the teeth when the model 715 is manipulated in the directions of arrows 811 or 812, as may be seen, for example, in FIG. 10. It should be understood that while in certain embodiments, this "flare out" features may be dependent upon user action and/or settings, in other embodiments such may be the default mode of the model 715, as may be desirable for particular applications. Is should also be understood that the "flare out" feature may be configured to function in either the "top" or "bottom" configurations 750, 760 as described elsewhere herein.

According to various embodiments, the "bottom open" configuration 760 of FIGS. 12-13 may be achieved by scrolling (e.g., via a mouse/cursor, touch, or the like) substantially downward on the model 715 in the direction indicated by arrow 820. In certain embodiments, as the scrolling in the direction indicated by arrow 820 occurs, the bottom teeth progressively hinge open, while the top teeth move upward within the model. It should be understood that in these and other embodiments, such a "dual motion" when scrolling in the direction indicated by arrow 820 enables opening of the bottom teeth without the need to resize the window in which the model 715 appears, much as described previously in the context of the "top open" configuration 750. In other words, the "dual motion" features of both configurations allow the view of model 715 to be smaller vertically yet still allow good visibility to the inside of the hinged opened set of teeth. Of course, in still other embodiments (see FIG. 15), in which the model window may be enlarged, such dual motion may be optional, as may be desirable for particular applications.

According to various embodiments, as may be seen in FIGS. 12-13, once placed into the "bottom open" configuration 760, the model 715 may be further manipulated by movement in the direction of arrows 822 and 824, facilitating viewing perspectives of the tooth model from left, right, and anywhere there-between, as may be desirable for particular applications. In certain embodiments, it should be noted that when in the "bottom open" configuration 760, the elastics 732, 737 passing between teeth 734, 736 (see also FIG. 17) may be configured to sequentially "snap" to successive discreet points upon the teeth (as previously described herein), so as to prevent the elastics 732, 737 from ever passing through the interior of the teeth, even during progressive opening of the bottom teeth relative to the upper teeth. In other embodiments, the manner in which the elastics 732, 737 snap to particular discreet points upon the teeth may be further configured such an the elastic 732, 737, upon opening or closing of the teeth model, wrap around the edge of the lower tooth 734 rather than passing through the body of the lower tooth.

In various embodiments, the successive discreet points are positioned along the incisal edges of the upper incisors and activated when elastic 732, 737 connects between two anterior teeth, one upper and one lower. In other embodiments, the successive discreet points are positioned along the posterior teeth, which allows posterior cross-bite elastics to wrap around the cusps of the upper and lower posterior teeth when connected from upper to lower with the connection passing from an inside to an outside tooth surface. Of course, still other embodiments may incorporate any of a variety of configurations, as associated with any of a variety of teeth located within the model 715, provided such similarly facilitate substantially preventing passage of elastics 732 through the interior of any teeth of the model 715.

With continued reference to FIGS. 12-13, it should be understood that in various embodiments, the "dual motion" feature described above, when hinging open the top teeth and moving downward the lower teeth, may be further configured so as to simultaneously "flare out" the "back teeth" portion of the model 715. As may be seen in at least FIG. 12, such movement may facilitate better visibility of the chewing surfaces of the teeth in the "bottom open" configuration 750, while also improving visibility of the inside of the teeth when the model 715 is manipulated in the directions of arrows 822 or 824, as may be seen, for example, in FIG. 13. It should be understood that while in certain embodiments, this "flare out" features may be dependent upon user action and/or settings, in other embodiments such may be the default mode of the model 715, as may be desirable for particular applications.

Still further, it should be understood from FIGS. 8-13, when viewed together, that the various manipulations of the 3-D model 715 in the directions of at least arrows 810, 820, 812, 811, 822, and 824 may be performed with the model oriented in any of the previously described configurations (e.g., closed, top open, bottom open, etc.). Of course, it should be further understood that any of a variety of movements may be imposed upon the model, for purposes of rotation, opening, or closing of the same, as may be desired for particular applications and such should be considered within the scope of the present invention.

Additional Features

Returning now with particular emphasis upon FIGS. 9 and 12, according to various embodiments, the interactive 3-D model 715 may be further configured with a zone 850, within which scrolling upward or downward (e.g. in the direction of arrows 810 or 820, as previously described herein) will not result in any manipulation of the model between the closed, top-open, and/or bottom open configurations. Such is particularly beneficial when performing scrolling functions in the reverse of that previously described herein, namely to close the teeth either by scrolling in the upward direction 810 while in the "bottom open" configuration or by scrolling in the downward direction 820 while in the "top open" configuration. In certain embodiments, the "dead" zone 850 is configured such that movement there-through by a user (e.g., via a mouse, via touch, or otherwise) will stop any ongoing manipulation of the model toward the closed configuration. In other embodiments, movement through the zone 850 will only momentarily pause ongoing manipulation of the model, after which if the user continues scrolling, manipulation will commence.

In other words, in any of these and other embodiments, the zone 850 is configured to substantially prevent "overshooting" of the opening and closing of the teeth of the model 715 (e.g., creating a biting motion). In still other embodiments, however, it should be understood that the zone 850 may be optional (e.g., selectively activated), where, for example, it may be useful for an orthodontist to rapidly and efficiently switch between the top open and bottom open configurations without any delay.

Relatedly, according to various embodiments, the interactive 3-D model 715 may be configured with a "self-closing" feature, wherein if a user pauses with the model manipulated such that the teeth are substantially nearly in the closed configuration 740, the model will automatically revert to the closed configuration. In other words, were a user to scroll upward in the direction of arrow 810 while trying to close the teeth from the "bottom open" configuration of FIG. 12, and in so doing not fully reach the closed configuration of FIG. 8, the model would, after a brief delay, automatically close the teeth. In certain embodiments, the auto or self-closing feature may be activated when a user passes through the "dead" zone 850 as previously described herein. In other embodiments, the auto or self-closing feature may be selectively activated, as may be desirable for particular applications. In still other embodiments, the auto or self-closing feature may be configured for use regardless of whether the model is in a left, center, or right-facing orientation (see FIGS. 12-13, for example).

According to various embodiments, the system 5 comprising the interactive 3-D model 715 may be configured to display a tooth model of a particular patient at more than a single point in time. While, as previously described herein, certain embodiments of the model 715 may be configured for display and manipulation of teeth, brackets, elastics, and the like as of the present day (see, for example, FIG. 8), other embodiments may be further configured to provide visualization one or more of the same features over a period of time. In any of these and still other embodiments, the period of time may be any portion or even the entirety of a patient's treatment plan (e.g., from inception to present day, from present day to future anticipated completion date, etc.). In those embodiments where the period of time is historical in nature, the visualization may be tied to a patient's historical treatment data, including such textual data as may be populated within field 707 (see FIG. 13). Similarly, in those embodiments where the period of time is futuristic in nature, the visualization may be tied to a proposed treatment plan for a patient (see, e.g., FIG. 13), thereby facilitating an understanding of how proposed treatment plan may progress, if pursued.

In any of these various embodiments of the model 715, the visualization over time may be provided in successively viewed still images (e.g., corresponding and/or associated with respective patient appointment dates). Of course, in other embodiments the model 715 may be configured to display a "time-lapse" visualization of the tooth model over a selected period. In any of these and still other embodiments, the model 715, when so configured for providing visualization over a period of time, may also visualize changes in any of a variety of elements included in the historical or proposed treatment plans, including the non-limiting examples of depicting changes in placement and/or relative locations of brackets, elastics, arch wires, and/or teeth. In at least one embodiment, the various elements may be at least initially displayed adjacent the model 715, with each being animated to move onto the model in an animated fashion, as the "time-lapse" visualization proceeds. In other embodiments, however, motion of the various elements and/or the imposed motion upon teeth as a result of placement of the various elements may be otherwise visually displayed so as to convey the impact of particular treatment plans over time. As a non-limiting example, the animated model may be configured to illustrate application of an expander upon certain teeth of patient "Maggie," whereby during continued time-lapse visualization thereof involves movement of the affected teeth apart relative to one another, as commonly known and understood in the art to be the effect of such types of hardware components.

In various embodiments of the model 715, whether visualizing over time or at a particular instance in time, the upper and lower teeth of the model may be, in their closed position (as previously described herein) juxtaposed so as to simulate various malocclusions of particular patients. In certain embodiments, other variations and/or medical conditions associated with particular patients may be likewise simulated via the model 715, as such may be beneficial for ensuring the accuracy and completeness of the model. In any of these and still other embodiments, if and when any teeth are extracted due to an existing or proposed treatment plan, the spaces created by such extraction may be likewise closed via the visualization over time, thereby further illustrating the impact of historical and/or proposed treatment techniques and actions.

According to various embodiments, the system 5 may be configured such that selection of any of the elements (e.g., brackets, elastics, retainers, expansion appliances, etc.) displayed on the interactive 3-D model 715 results in a corresponding change in an inventory count for such elements within the system (e.g., in the data module 400 or an inventory table associated therewith). In certain embodiments, updates to the inventory table and/or data module 400 information may be tied more specifically to a user saving (e.g., finalizing) selections of elements for a particular treatment appointment. Of course, in other embodiments, updates to the data module may be otherwise configured, as may be desirable for particular applications. In still other embodiments, it should be understood that various features of the model 715 may be likewise associated with various remaining features of the admin module 500 and the clinical module 700 of the system 5, as have been described previously herein.

Report Tool 780 & Report (sub)Module 790

Returning now to FIGS. 8-14 and with particular emphasis upon FIG. 8, the interactive 3-D model 715 and/or its associated screen display 711 may be configured further with a report tool 780 associated with the report module 790 (see FIG. 2) for generating any of a variety of correspondence from the system 5. In certain embodiments, selection and/or activation of the report tool 780 may be configured to display a new screen 791 (see FIG. 16), which provides a variety of options for the subject 792, content 793, editing, and delivery methods for the desired correspondence. Once a user selects the desired content and associated data for delivery, an icon 794 may be selected to transmit the same to any of a variety of individuals, including the non-limiting examples of patient, account holders (e.g., guardians or parents), insurance providers, and/or referral recipients.

With particular reference now to FIGS. 16 and 18, in various embodiments, at least a portion of the content 793 selectable with the report tool 780 may be indicative of images 796 of respective left, center, and right views of a patient's latest 3-D model 715, together with details regarding the type of elastics 797 placed thereon (see specifically FIG. 18). In certain embodiments, such visual data of elastic type and placement may be emailed as at least a portion of an instructive report 795, 795, which may be provided to a patient and/or their guardian or parent, for use as a convenient reference or reminder regarding proper placement of elastics between successive orthodontic appointments. In other embodiments, the visual data may be accompanied by any portion of the data illustrated on screen displays 791 and 795 of FIGS. 16-17, or still further any portion of data contained within module 400, as may be desirable for particular applications. Still further, it should be understood that while the visual images 796 of FIG. 18 are represented in a closed-teeth configuration, as has been described previously herein, such may additionally or even alternatively be transmitted in a top or bottom open configuration (or even a partially open configuration, or the like), as may be desirable or beneficial for a particular application, such as when, for example cross-bite or other elastics that may pass from an inside tooth surface to an outside tooth surface, must be viewable by the patient via nothing more than the email or printout visualization.

With continued reference momentarily to FIG. 17, it should further be appreciated that any of the exemplary instructive reports 795, 795A, as may be generated via the report module 790 according to various embodiments, may include not only visual illustrations (see 799), as previously described, but also textual educational material 798 providing reminders, advice, and the like to patients, whether reinforcing information conveyed during appointments or otherwise. It should be understood that while visual illustrations 799 of FIG. 17 may be provided via traditionally known and understood teeth charts, such may be either supplemented by or replaced with the images 796 so as to provide a more useful tool for patient visualization of maintenance actions to be performed between successive appointments, or however may be desirable.

Conclusion

The foregoing description of the various embodiments of the present invention has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

That which is claimed:

1. A computer-implemented method for dynamically manipulating a three-dimensional virtual model representing a patient's teeth so as to facilitate visualization of an orthodontic treatment plan being applied thereto, said method comprising the steps of:

rendering said three-dimensional virtual model based, at least in part, upon one or more images of a patient's teeth, said three-dimensional virtual model comprising a plurality of teeth, said plurality of teeth comprising two sets of oppositely-oriented teeth; and manipulating said three-dimensional virtual model via a translational movement in a two-dimensional computer display area and along a plane vertically oriented relative to said oppositely-oriented teeth, wherein said translational movement is configured to simultaneously impose a translational manipulation upon a first one of the two sets of oppositely oriented teeth and a rotational manipulation upon a second one of the two sets of oppositely oriented teeth, said simultaneous manipulation being configured to open said two sets of oppositely oriented teeth relative to one another so as to facilitate visualization of an orthodontic treatment plan for the patient's teeth.

2. The computer-implemented method of claim 1, wherein:
said two sets of oppositely-oriented teeth comprise a set of top teeth and a set of lower teeth;
said translational movement in a vertical plane is in a first direction, said first direction being oriented toward said set of top teeth; and
said translational movement in said first direction imposes said translational manipulation upon said set of top teeth and said rotational manipulation upon said lower teeth.

3. The computer-implemented method of claim 1, wherein:
said two sets of oppositely-oriented teeth comprise a set of top teeth and a set of lower teeth;
said translational movement in a vertical plane is in a second direction, said second direction being oriented toward said set of lower teeth; and
said translational movement in said second direction imposes said rotational manipulation upon said set of top teeth and said translational manipulation upon said lower teeth.

4. The computer-implemented method of claim 1, further comprising the step of expanding at least a portion of one of the two sets of oppositely oriented teeth outwardly relative to the other of the two sets of oppositely oriented teeth, said outward expanding occurring in a direction substantially perpendicular to said translational and rotational manipulations imposed upon said two sets of oppositely oriented teeth.

5. The computer-implemented method of claim 4, wherein said two sets of oppositely-oriented teeth comprise a set of top teeth and a set of lower teeth and said outward expanding is of a back portion of said set of top teeth.

6. The computer-implemented method of claim 4, wherein said two sets of oppositely-oriented teeth comprise a set of top teeth and a set of lower teeth and said outward expanding is of a back portion of said set of bottom teeth.

7. The computer-implemented method of claim 1, further comprising the step of at least temporarily suspending said translational and rotational manipulations imposed upon said three-dimensional virtual model when said one or more movements in said two-dimensional computer display area travel through a location substantially intermediate said two sets of oppositely-oriented teeth.

8. The computer-implemented method of claim 1, further comprising the step of automatically closing said two sets of oppositely-oriented teeth when said one or more movements in said two-dimensional computer display area pause for a period of time within a location substantially intermediate said two sets of oppositely-oriented teeth.

9. The computer-implemented method of claim 1, further comprising the step of placing one or more orthodontic hardware elements upon one or more teeth within said two sets of oppositely-oriented teeth.

10. The computer-implemented method of claim 1, further comprising, subsequent to said placing at least one orthodontic hardware element upon at least one tooth within said two sets of oppositely-oriented teeth, automatically placing the same said orthodontic hardware element upon at least one additional tooth upon selection of said at least one additional tooth within a predetermined time period from said initial placement.

11. The computer-implemented method of claim 10, wherein said predetermined time period is approximately 1.5 seconds.

12. The computer-implemented method of claim 9, wherein said one or more orthodontic hardware elements are selected from the group consisting of: brackets, elastics, arch-wires, retainers, expansion appliances, and trans-palatal bars.

13. The computer-implemented method of claim 9, wherein said one or more orthodontic hardware elements comprise one or more elastics and said method further comprises the step of automatically manipulating the visualization of said one or more elastics relative to said two sets of oppositely-oriented teeth, such that during said translational and rotational manipulations thereof, no portion of said one or more elastics travels through an interior portion of said teeth.

14. The computer-implemented method of claim 9, wherein said one or more elastics do not travel through said interior portions of said teeth due at least in part to one or more portions of said one or more elastics being configured to automatically sequentially snap to sequentially positioned discrete points along said teeth.

15. The computer-implemented method of claim 9, wherein said one or more orthodontic hardware elements comprise one or more elastics and said method further comprises the step of placing said one or more elastics relative to two or more teeth within said two sets of oppositely-oriented teeth, such that said one or more elastics are strung between said two or more teeth in a predetermined configuration.

16. The computer-implemented method of claim 1, wherein data associated with said orthodontic treatment plan is operatively associated with said three dimensional virtual model and said method further comprises the step of generating a time-lapse visualization of said movements imposed upon said patient's teeth at least in part due to one or more orthodontic hardware elements being placed thereon during said orthodontic treatment plan.

17. The computer-implemented method of claim 1, further comprising the steps of generating and transmitting a representation of said three-dimensional virtual model to said patient for said patient's reference between successive orthodontic appointments.

18. The computer-implemented method of claim 17, wherein said three-dimensional virtual model comprises one or more elastics strung between one or more of said plurality of teeth, such that said representation is configured to assist said patient with subsequent maintenance of said one or more elastics between successive orthodontic appointments.

19. A computer-implemented method for dynamically manipulating a three-dimensional virtual model representing a patient's teeth so as to facilitate visualization of an orthodontic treatment plan being applied thereto, said method comprising the steps of:
rendering said three-dimensional virtual model based, at least in part, upon one or more images of a patient's teeth, said three-dimensional virtual model comprising a plurality of teeth, said plurality of teeth comprising two sets of oppositely-oriented teeth;
sequencing said three-dimensional virtual model through two or more of a plurality of discrete points in time, wherein each of said plurality of points in time is associated with data indicative of a discrete point in time of said orthodontic treatment plan, such that said three-dimensional virtual model is manipulated based at least in part thereon during said sequencing through said two or more of said plurality of discrete points in time; and selectively pausing said sequencing and manipulating said three-dimensional virtual model via a translational movement in a plane vertically oriented relative to said oppositely-oriented teeth, wherein said translational movement is configured to simultaneously impose a translational manipulation upon a first one of the two sets of oppositely oriented teeth and a rotational manipulation upon a second one of the two sets of oppositely oriented teeth, said simultaneous manipulation being configured to open said two sets of oppositely oriented teeth relative to one another so as to facilitate visualization of an orthodontic treatment plan for the patient's teeth.

20. The computer-implemented method of claim 19, wherein at least a portion of said plurality of points in time are historical relative to a current time so as to represent a previously executed orthodontic treatment plan.

21. The computer-implemented method of claim 19, wherein at least a portion of said plurality of points in time are historical relative to a current time, at least a portion of said plurality of points in time are futuristic relative to said current time, such that during said sequencing step, said one or more images of said patient's teeth are sequenced through said plurality of historical points in time and said three-dimensional virtual model is sequenced through said plurality of futuristic points in time.

22. The computer-implemented method of claim 19, wherein said sequencing occurs automatically across successive points in time so as to generate a time-lapse visualization of the progress of said orthodontic treatment plan.

23. The computer-implemented method of claim 22, wherein said time-lapse visualization illustrates placement of one or more orthodontic hardware elements upon one or more teeth within said two sets of oppositely-oriented teeth and said sequencing step illustrates movement imposed upon said one or more teeth at least in part by said one or more orthodontic hardware elements over time.

24. The computer-implemented method of claim 23, wherein said one or more orthodontic hardware elements are selected from the group consisting of: brackets, elastics, arch-wires, retainers, expansion appliances, and trans-palatal bars.

25. A computer-implemented method for dynamically manipulating a three-dimensional virtual model representing a patient's teeth so as to facilitate visualization of an orthodontic treatment plan being applied thereto, said method comprising the steps of:

rendering said three-dimensional virtual model based, at least in part, upon one or more images of a patient's teeth, said three-dimensional virtual model comprising a plurality of teeth, said plurality of teeth comprising two sets of oppositely-oriented teeth;

placing one or more orthodontic hardware elements upon one or more teeth within said two sets of oppositely-oriented teeth;

manipulating said three-dimensional virtual model via a translational movement in a two-dimensional computer display area and along a plane vertically oriented relative to said oppositely-oriented teeth, wherein said translational movement is configured to simultaneously impose a translational manipulation upon a first one of the two sets of oppositely oriented teeth and a rotational manipulation upon a second one of the two sets of oppositely oriented teeth, said simultaneous manipulation being configured to open said two sets of oppositely oriented teeth relative to one another so as to facilitate visualization of an orthodontic treatment plan for the patient's teeth;

generating a representation of said three-dimensional virtual model, said representation comprising at least one illustration obtained via said simultaneous manipulation of said two sets of oppositely-oriented teeth and said one or more orthodontic hardware elements placed thereon; and transmitting said representation of said three-dimensional virtual model to said patient for access thereof via an interface for said patient's reference between successive orthodontic appointments.

26. The computer-implemented method of claim 25, wherein said one or more hardware elements comprises one or more elastics and said representation of said three-dimensional virtual model further comprises textual instructions for patient placement of said one or more elastics alongside said visualization of said placement of said one or more elastics in said three-dimensional virtual model.

27. The computer-implemented method of claim 25, further comprising the steps of capturing two or more screen shots of said three-dimensional virtual model from two or more angles obtained via said simultaneous manipulation imposed upon said three-dimensional virtual model, and embedding said at least said two or more screen shots of said three-dimensional virtual model within said representation.

28. The computer-implemented method of claim 27, wherein said two or more screen shots comprise a left facing screen shot, a front facing screen shot, and a right facing screen shot relative to said two sets of oppositely oriented teeth.

29. The computer-implemented method of claim 25, wherein said representation is electronically transmitted to at least said patient.

* * * * *

UNITED STATES PATENT AND TRADEMARK OFFICE
CERTIFICATE OF CORRECTION

PATENT NO.         : 9,510,918 B2                                    Page 1 of 1
APPLICATION NO.    : 13/875578
DATED              : December 6, 2016
INVENTOR(S)        : Sanchez It is certified that error appears in the above-identified patent and that said Letters Patent is hereby corrected as shown below:

On the Title Page

Item (71): delete "Cogent Design, Inc." and insert --Cogent Design, Inc. dba tops Software--

Item (73): delete "Cogent Design, Inc." and insert --Cogent Design, Inc. dba tops Software--

Signed and Sealed this
Second Day of May, 2017

Michelle K. Lee
*Director of the United States Patent and Trademark Office*